(12) United States Patent
Krishnaswami et al.

(10) Patent No.: US 10,937,522 B2
(45) Date of Patent: Mar. 2, 2021

(54) SYSTEMS AND METHODS FOR ANALYSIS AND INTERPRETATION OF NUCLIEC ACID SEQUENCE DATA

(71) Applicant: LIFE TECHNOLOGIES CORPORATION, Carlsbad, CA (US)

(72) Inventors: Brijesh Krishnaswami, San Mateo, CA (US); Yuandan Lou, Cupertino, CA (US); Asim Siddiqui, San Francisco, CA (US); Heinz Breu, Palo Alto, CA (US); Amitabh Shukla, San Jose, CA (US); Karl Kuhlmann, Menlo Park, CA (US)

(73) Assignee: Life Technologies Corporation, Carlsbad, CA (US)

( * ) Notice: Subject to any disclaimer, the term of this patent is extended or adjusted under 35 U.S.C. 154(b) by 95 days.

(21) Appl. No.: 16/211,609

(22) Filed: Dec. 6, 2018

(65) Prior Publication Data
US 2019/0172549 A1 Jun. 6, 2019

Related U.S. Application Data

(63) Continuation of application No. 14/749,257, filed on Jun. 24, 2015, now abandoned, which is a continuation of application No. 13/648,998, filed on Oct. 10, 2012, now abandoned.

(60) Provisional application No. 61/640,389, filed on Apr. 30, 2012, provisional application No. 61/598,499, filed on Feb. 14, 2012, provisional application No. 61/545,922, filed on Oct. 11, 2011, provisional application No. 61/545,895, filed on Oct. 11, 2011.

(51) Int. Cl.
*G16B 20/00* (2019.01)
*G06F 16/9038* (2019.01)
*G16B 50/00* (2019.01)

(52) U.S. Cl.
CPC ......... *G16B 20/00* (2019.02); *G06F 16/9038* (2019.01); *G16B 50/00* (2019.02)

(58) Field of Classification Search
CPC ...... G16B 20/00; G16B 50/00; G06F 16/9038
See application file for complete search history.

(56) References Cited

U.S. PATENT DOCUMENTS

| | | |
|---|---|---|
| 2003/0036087 A1 | 2/2003 | Kaushikkar et al. |
| 2003/0113727 A1 | 6/2003 | Girn et al. |
| 2003/0175722 A1 | 9/2003 | Mann et al. |
| 2004/0005610 A1 | 1/2004 | Sampath |
| 2004/0220897 A1 | 11/2004 | Bernhart et al. |
| 2005/0032095 A1 | 2/2005 | Wigler et al. |
| 2006/0020886 A1 | 1/2006 | Agrawal et al. |

(Continued)

OTHER PUBLICATIONS

Cawsey et al., "Natural Language Generation in Health Care", Journal of the American Medical Informatics Association, vol. 4, No. 6, pp. 473-482 (1997).

(Continued)

*Primary Examiner* — Jensen Hu

(57) ABSTRACT

Systems and method for annotating variants within a genome can call variants from reads or receive called variants directly and associate the called variants with functional annotations and interpretive annotations. A summary report of the called variants, the associated functional annotations, and the associated interpretive annotations can be generated.

18 Claims, 15 Drawing Sheets

(56) References Cited

U.S. PATENT DOCUMENTS

| | | | |
|---|---|---|---|
| 2006/0068405 | A1 | 3/2006 | Diber et al. |
| 2007/0027630 | A1 | 2/2007 | Sanchez et al. |
| 2007/0038385 | A1 | 2/2007 | Nikolskaya et al. |
| 2007/0169021 | A1 | 7/2007 | Huynh et al. |
| 2007/0207481 | A1 | 9/2007 | Wigler et al. |
| 2008/0228703 | A1 | 9/2008 | Kenedy et al. |
| 2009/0026082 | A1 | 1/2009 | Rothberg et al. |
| 2009/0127589 | A1 | 5/2009 | Rothberg et al. |
| 2009/0156906 | A1 | 6/2009 | Liebman et al. |
| 2009/0254572 | A1 | 10/2009 | Redlich et al. |
| 2009/0259451 | A1 | 10/2009 | Senger et al. |
| 2011/0021378 | A1 | 1/2011 | Callewaert et al. |
| 2011/0189663 | A1 | 8/2011 | Cotterchio et al. |
| 2011/0257896 | A1 | 10/2011 | Dowds et al. |
| 2011/0282876 | A1 | 11/2011 | Tchagang |
| 2011/0289441 | A1 | 11/2011 | Venon et al. |
| 2012/0102054 | A1* | 4/2012 | Popescu ............... G16B 40/00 707/754 |
| 2012/0110013 | A1 | 5/2012 | Conde et al. |
| 2013/0013213 | A1* | 1/2013 | Worthey ............... G16B 20/00 702/19 |
| 2013/0091126 | A1 | 4/2013 | Krishnaswami et al. |
| 2013/0332081 | A1 | 12/2013 | Reese et al. |
| 2014/0280327 | A1* | 9/2014 | Pham ............... G16B 50/30 707/770 |
| 2015/0095064 | A1* | 4/2015 | Schols ............... G16H 10/60 705/3 |
| 2015/0259744 | A1 | 9/2015 | Begovich et al. |

OTHER PUBLICATIONS

Ge, Dongliang et al., "SVA: software for annotating and visualizing sequenced human genomes", Bioinformatics vol. 27, No. 14, 2011, 1998-2000.

Kent, W et al., "Assembly of the Working Draft of the Human Genome with GigAssembler", Genome Research, vol. 11, 2001, pp. 1541-1548.

Lee, Phil et al., "F-SNP: computationally predicted functional SNPs for disease association studies", Nucleic Acids Research vol. 36, Database issue, 2008, D820-D824.

Mullikin, J et al., "The Phusion Assembler", Genome Research, vol. 13, 2003, pp. 81-90.

PCT/US2012/059601, International Preliminary Report on Patentability, dated Apr. 24, 2014, 13 pages.

PCT/US2012/059601, International Search Report dated Jul. 12, 2013, 9 pages.

PCT/US2012/059601, International Written Opinion dated Jul. 12, 2013, 13 pages.

PCT/US2012/059601, Partial International Search Report dated Jan. 17, 2013, 7 pages.

Pico et al., "SNPLogic: an interactive single nucleotide polymorphism selection, annotation, and prioritization system", Nucleic Acids Research, vol. 37, Database issue, pp. D803-D809 (2009).

Roach, Jet al., "Pairwise End Sequencing: A Unified Approach to Genomic Mapping and Sequencing", Genomics, vol. 26, 1995, pp. 345-353.

Sambrook et al., "Molecular Cloning: A Laboratory Manual", Third ed., Cold Spring Harbor Laboratory Press, Cold Spring Harbor, N.Y., 2000, cover pages and table of contents, 25 pages.

Siegel, Andrew et al., "Modeling the Feasibility of Whole Genome Shotgun Sequencing Using a Pairwise End Strategy", Genomics, 68, 2000, 237-246.

Torkamani et al., "Annotating individual human genomes", Genomics, vol. 98, No. 4, pp. 233-241 (2011).

Wang et al., "ANNOVAR: functional annotation of genetic variants from high-throughput sequencing data", Nucleic Acids Research, vol. 38, No. 16, pp. 1-7 (2010).

* cited by examiner

SYSTEMS AND METHODS FOR ANALYSIS AND INTERPRETATION OF NUCLIEC ACID SEQUENCE DATA

RELATED APPLICATIONS

This application is a continuation of U.S. patent application Ser. No. 14/749,257 filed Jun. 24, 2015, which is a continuation of U.S. patent application Ser. No. 13/648,998 filed Oct. 10, 2012 (now abandoned), which claims priority to U.S. Patent Application No. 61/640,389 filed Apr. 30, 2012, U.S. Patent Application No. 61/598,499 filed Feb. 14, 2012, U.S. Patent Application No. 61/545,922 filed Oct. 11, 2011, and U.S. Patent Application No. 61/545,895 filed Oct. 11, 2011, all of which disclosures are herein incorporated by reference in their entirety.

FIELD

The present disclosure generally relates to nucleic acid sequence data and in particular to user interfaces, systems and methods for annotating genomic variants detected in the nucleic acid sequence data.

INTRODUCTION

Upon completion of the Human Genome Project, one focus of the sequencing industry has shifted to finding higher throughput and/or lower cost nucleic acid sequencing technologies, sometimes referred to as "next generation" sequencing (NGS) technologies. In making sequencing higher throughput and/or less expensive, the goal is to make the technology more accessible for sequencing. These goals can be reached through the use of sequencing platforms and methods that provide sample preparation for larger quantities of samples of significant complexity, sequencing larger numbers of complex samples, and/or a high volume of information generation and analysis in a short period of time. Various methods, such as, for example, sequencing by synthesis, sequencing by hybridization, and sequencing by ligation are evolving to meet these challenges.

Research into fast and efficient nucleic acid (for example, genome, exome, etc.) sequence assembly methods is vital to the sequencing industry as NGS technologies can provide ultra-high throughput nucleic acid sequencing. As such sequencing systems incorporating NGS technologies can produce a large number of short sequence reads in a relatively short amount time. Sequence assembly methods must be able to assemble and/or map a large number of reads quickly and efficiently, such as by minimizing use of computational resources. For example, the sequencing of a human size genome can result in tens or hundreds of millions of reads that need to be assembled before they can be further analyzed to determine their biological, diagnostic and/or therapeutic relevance.

Exemplary applications of NGS technologies include, but are not limited to: genomic variant (for example, indels, copy number variations, single nucleotide polymorphisms, etc.) detection, resequencing, gene expression analysis and genomic profiling.

A wealth of nucleic acid sequence information is now available in sequence databases, both public and private. For example, public databases of metabolic, genetic and physiological pathways of various organisms (for example, Munich Information Center for Protein Sequences (MIPS), NCBI's Single Nucleotide Polymorphism database (dbSNP), etc.) and some genes (for example, Kyoto Encyclopedia of Genes and Genomes (KEGG), etc.) have been developed largely from the published literature of many traditional low throughput experimental studies. An advantage of this abundance of data is that improved diagnostic testing and genomics guided therapeutic regimens (for example, drugs, surgery, radiation therapy, medical devices, diet, psychiatric therapy, etc.) will be possible as new information about how an individuals' genetic and epigenetic profile correlates to risk factors for disease, drug targets, protein therapeutics, devices, treatment protocols, and the like are identified and characterized. In addition, because relatively small differences in the genetic makeup (genotype), gene expression, or epigenetic status of individuals can result in large differences in physical characteristics (phenotype), some diagnostic testing and therapeutic regimens may work better with some individuals than with others, and in some cases deleterious effects can be avoided. With knowledge of how different genotypes or other genetic and epigenetic factors affect the function of an individual's various biological pathways (for example, metabolic, signaling, regulation, etc.), diagnostic tests and treatment regimens can potentially be customized based on genetic and epigenetic information associated with the specific individual being treated.

While the quantity of nucleic acid sequence data that one can gather using conventional sequencing techniques is very large, it can often not be presented or analyzed in the most useful context. The diagnostic and therapeutic relevance of genetic and epigenetic data can often be best determined by its relationship to other pieces of information. For example, knowing that a particular genetic mutation (for example, SNP, Indel, CNV, etc.) affects a particular metabolic or physiological pathway that plays a role in or otherwise affects the inception, progression, or treatment of a particular disease can be clinically important information. In addition, there is a need to correlate this data with various types of clinical data, for example, a patient's age, sex, weight, stage of clinical development, stage of disease progression, etc.

Conventional techniques do not facilitate easy correlation of candidate gene mutations with the wealth of information that is currently available that can provide functional or interpretive context to the mutations. This is due to the enormous amount of information being generated by researchers and the lack of adequate tools to organize the information in a manner which facilitates analysis of the same.

As such, there is a need for user friendly interfaces and methods to allow easy analysis and interpretation of genomic variant candidates identified in nucleic acid sequencing data.

DRAWINGS

For a more complete understanding of the principles disclosed herein, and the advantages thereof, reference is now made to the following descriptions taken in conjunction with the accompanying drawings, in which.

Figure 1:
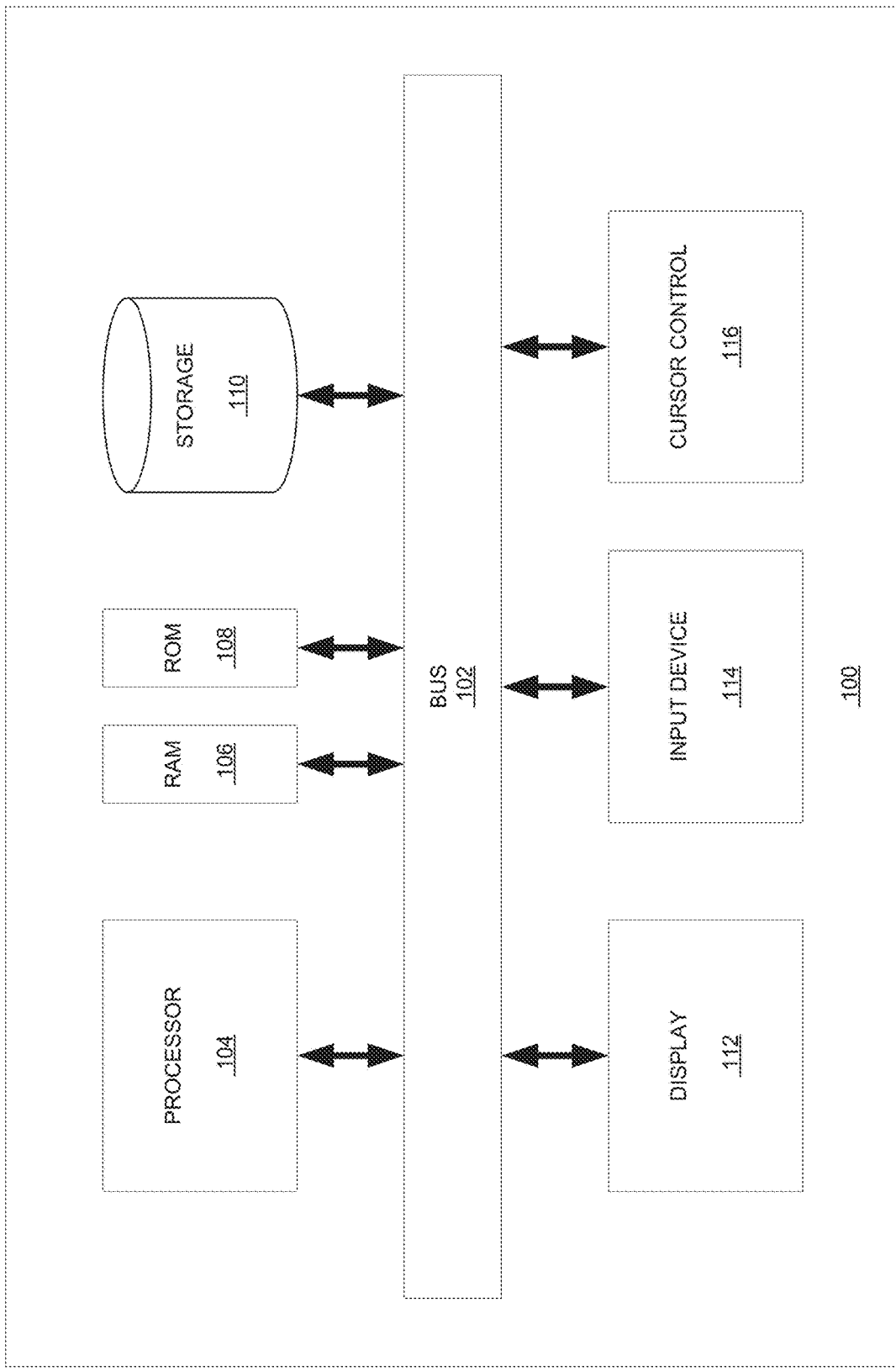
FIG. 1 is a block diagram that illustrates a computer system, in accordance with various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DESCRIPTION OF VARIOUS EMBODIMENTS

Embodiments of user interfaces and methods for analyzing and interpreting nucleic acid sequence data are described herein.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

It will be appreciated that there is an implied "about" prior to the temperatures, concentrations, times, number of bases, coverage, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, for example, Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques described herein are those well known and commonly used in the art.

As used herein, "a" or "an" means "at least one" or "one or more."

A "system" may be used to denote a set of components, real or abstract, comprising a whole where each component interacts with or is related to at least one other component within the whole.

A "biomolecule" may be used to denote any molecule that is produced by a biological organism, including large polymeric molecules such as proteins, polysaccharides, lipids, and nucleic acids (DNA and RNA) as well as small molecules such as primary metabolites, secondary metabolites, and other natural products.

The phrase "next generation sequencing" or NGS refers to sequencing technologies having increased throughput as compared to traditional Sanger- and capillary electrophoresis-based approaches, for example with the ability to generate hundreds of thousands of relatively small sequence reads at a time. Some examples of next generation sequencing techniques include, but are not limited to, sequencing by synthesis, sequencing by ligation, and sequencing by hybridization. More specifically, the Personal Genome Machine (PGM) of Life Technologies Corp. provides massively parallel sequencing with enhanced accuracy. The PGM System and associated workflows, protocols, chemistries, etc. are described in more detail in U.S. Patent Application Publication No. 2009/0127589 and No. 2009/0026082, the entirety of each of these applications being incorporated herein by reference.

The phrase "sequencing run" refers to any step or portion of a sequencing experiment performed to determine some information relating to at least one biomolecule (for example, nucleic acid molecule).

It is well known that DNA (deoxyribonucleic acid) is a chain of nucleotides consisting of 4 types of nucleotides; A (adenine), T (thymine), C (cytosine), and G (guanine), and that RNA (ribonucleic acid) is comprised of 4 types of nucleotides; A, U (uracil), G, and C. It is also known that certain pairs of nucleotides specifically bind to one another in a complementary fashion (called complementary base pairing). That is, adenine (A) pairs with thymine (T) (in the case of RNA, however, adenine (A) pairs with uracil (U)), and cytosine (C) pairs with guanine (G). When a first nucleic acid strand binds to a second nucleic acid strand made up of nucleotides that are complementary to those in the first strand, the two strands bind to form a double strand. As used herein, "nucleic acid sequencing data," "nucleic acid sequencing information," "nucleic acid sequence," "genomic sequence," "genetic sequence," or "fragment sequence," or "nucleic acid sequencing read" denotes any information or data that is indicative of the order of the nucleotide bases (for example, adenine, guanine, cytosine, and thymine/uracil) in a molecule (for example, whole genome, whole transcriptome, exome, oligonucleotide, polynucleotide, fragment, etc.) of DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

The phrase "base space" refers to a nucleic acid sequence data schema where nucleic acid sequence information is represented by the actual nucleotide base composition of the nucleic acid sequence. For example, the nucleic acid sequence "ATCGA" is represented in base space by the actual nucleotide base identities (for example, A, T/or U, C, G) of the nucleic acid sequence.

The phrase "flow space" refers to a nucleic acid sequence data schema wherein nucleic acid sequence information is represented by nucleotide base identifications (or identifications of known nucleotide base flows) coupled with signal or numerical quantification components representative of nucleotide incorporation events for the nucleic acid sequence. The quantification components may be related to the relative number of continuous base repeats, such as homopolymers, whose incorporation is associated with a respective nucleotide base flow. For example, the nucleic acid sequence "ATTTGA" may be represented by the nucleotide base identifications A, T, G and A (based on the nucleotide base flow order) plus a quantification component for the various flows indicating base presence/absence as well as possible existence of homopolymers. Thus for "T" in the example sequence above, the quantification component may correspond to a signal or numerical identifier of greater magnitude than would be expected for a single "T" and may be resolved to indicate the presence of a homopolymer stretch of "T"s (in this case a 3-mer) in the "ATTTGA" nucleic acid sequence.

A "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, for example 3-4, to several hundreds of monomeric units. Whenever a polynucleotide such as an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

The phrase "genomic variants" or "genome variants" denote a single or a grouping of sequences (in DNA or RNA) that have undergone changes as referenced against a particular species or sub-populations within a particular species due to mutations, recombination/crossover or genetic drift. Examples of types of genomic variants include, but are not limited to: single nucleotide polymorphisms (SNPs), copy number variations (CNVs), insertions/deletions (Indels), inversions, etc.

Genomic variants can be identified using a variety of techniques, including, but not limited to: array-based methods (for example, DNA microarrays, etc.) and whole or targeted nucleic acid sequencing. With nucleic acid sequencing, coverage data can be available at single base resolution. Nucleic acid sequencing systems such as the Life Technologies/Ion Torrent Personal Genome Machine (PGM) and Applied Biosystems SOLID™ Sequencing System can be used to sequence nucleic acid samples (for example human tissue/cell samples) which can include a test (or candidate) sample and a reference (or normal) sample.

In various embodiments, genomic variants can be detected using a nucleic acid sequencing system and/or analysis of sequencing data. The sequencing workflow can begin with the test sample being sheared or digested into hundreds, thousands or millions of smaller fragments which are sequenced on a nucleic acid sequencer to provide hundreds, thousands or millions of sequence reads, such as nucleic acid sequence reads. Each read can then be mapped to a reference or target genome, and in the case of mate-pair fragments, the reads can be paired thereby allowing interrogation of repetitive regions of the genome. The results of mapping and pairing can be used as input for various standalone or integrated genome variant (for example, SNP, CNV, Indel, inversion, etc.) analysis tools.

When genome variants are initially identified in nucleic acid samples, especially during analysis of disease-associated genes, their functional implications might not be immediately evident. Distinguishing between a genomic variant that changes the phenotype and one that does not is a difficult task. An increasing amount of evidence indicates that genomic variants in both coding and non-coding sequences can have unexpected deleterious effects on the splicing of a gene transcript. This makes distinguishing between benign polymorphisms and disease-associated splicing mutations difficult. Therefore, the ability to link the genetic variants identified in a nucleic acid sequence to various pieces of relevant biological information can greatly assist in the determination of the biological significance of the identified genetic variants.

The phrase "functional annotation" denotes data and information that can be relevant to the role that a called variant plays in gene/transcript/protein level function.

The phrase "coding region" denotes the portion of a gene's DNA or RNA, composed of exons that codes for protein. It should be understood, however, that the coding region of mRNA does not typically include the first part of the first exon (the 5' untranslated region) or the last part of the last exon (the 3' untranslated region).

The phrase "intragenic region," "intronic region," or "intron" denotes any nucleotide sequence within a gene that is removed by RNA splicing to generate the final mature RNA product of a gene.

The phrase "intergenic region" denotes a stretch of DNA sequences located between genes that contain few or no genes.

The phrase "sample genome" can denote a whole or partial genome of an organism.

The techniques of "paired-end," "pairwise," "paired tag," or "mate pair" sequencing are generally known in the art of molecular biology (Siegel A. F. et al., Genomics. 2000, 68: 237-246; Roach J. C. et al., Genomics. 1995, 26: 345-353). These sequencing techniques can allow the determination of multiple "reads" of sequence, each from a different place on a single polynucleotide. Typically, the distance between the two reads, such as the insert region, or other information regarding a relationship between the reads is known. In some situations, these sequencing techniques provide more information than does sequencing two stretches of nucleic acid sequences in a random fashion. With the use of appropriate software tools for the assembly of sequence information (for example, Millikin S. C. et al., Genome Res. 2003, 13: 81-90; Kent, W. J. et al., Genome Res. 2001, 11: 1541-8) it is possible to make use of the knowledge that the "paired-end," "pairwise," "paired tag" or "mate pair" sequences are not completely random, but are known to occur a known distance apart and/or to have some other relationship, and are therefore linked or paired in the genome. This information can aid in the assembly of whole nucleic acid sequences into a consensus sequence.

Computer-Implemented System

FIG. 1 is a block diagram that illustrates a computer system 100, upon which embodiments of the present teachings may be implemented. In various embodiments, computer system 100 can include a bus 102 or other communication mechanism for communicating information, and a processor 104 coupled with bus 102 for processing information. In various embodiments, computer system 100 can also include a memory 106, which can be a random access memory (RAM) or other dynamic storage device, coupled to bus 102 for determining base calls, and instructions to be executed by processor 104. Memory 106 also can be used for storing temporary variables or other intermediate information during execution of instructions to be executed by processor 104. In various embodiments, computer system 100 can further include a read only memory (ROM) 108 or other static storage device coupled to bus 102 for storing static information and instructions for processor 104. A storage device 110, such as a magnetic disk or optical disk, can be provided and coupled to bus 102 for storing information and instructions.

In various embodiments, computer system 100 can be coupled via bus 102 to a display 112, such as a cathode ray tube (CRT) or liquid crystal display (LCD), for displaying information to a computer user. An input device 114, including alphanumeric and other keys, can be coupled to bus 102 for communicating information and command selections to processor 104. Another type of user input device is a cursor control 116, such as a mouse, a trackball or cursor direction keys for communicating direction information and command selections to processor 104 and for controlling cursor movement on display 112. This input device typically has two degrees of freedom in two axes, a first axis (for example, x) and a second axis (for example, y), that allows the device to specify positions in a plane.

A computer system 100 can perform the present teachings. Consistent with certain implementations of the present teachings, results can be provided by computer system 100 in response to processor 104 executing one or more sequences of one or more instructions contained in memory 106. Such instructions can be read into memory 106 from another computer-readable medium, such as storage device 110. Execution of the sequences of instructions contained in memory 106 can cause processor 104 to perform the processes described herein. Alternatively hard-wired circuitry can be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium can take many forms, including but not limited to, non-volatile media, volatile media, and transmission media. Examples of non-volatile media can include, but are not limited to, optical or magnetic disks, such as storage device 110. Examples of volatile media can include, but are not limited to, dynamic memory, such as memory 106. Examples of transmission media can include, but are not limited to, coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

Nucleic Acid Sequencing Platforms

Nucleic acid sequence data can be generated using various techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, fluorescent-based detection systems, single molecule methods, etc.

Figure 2:
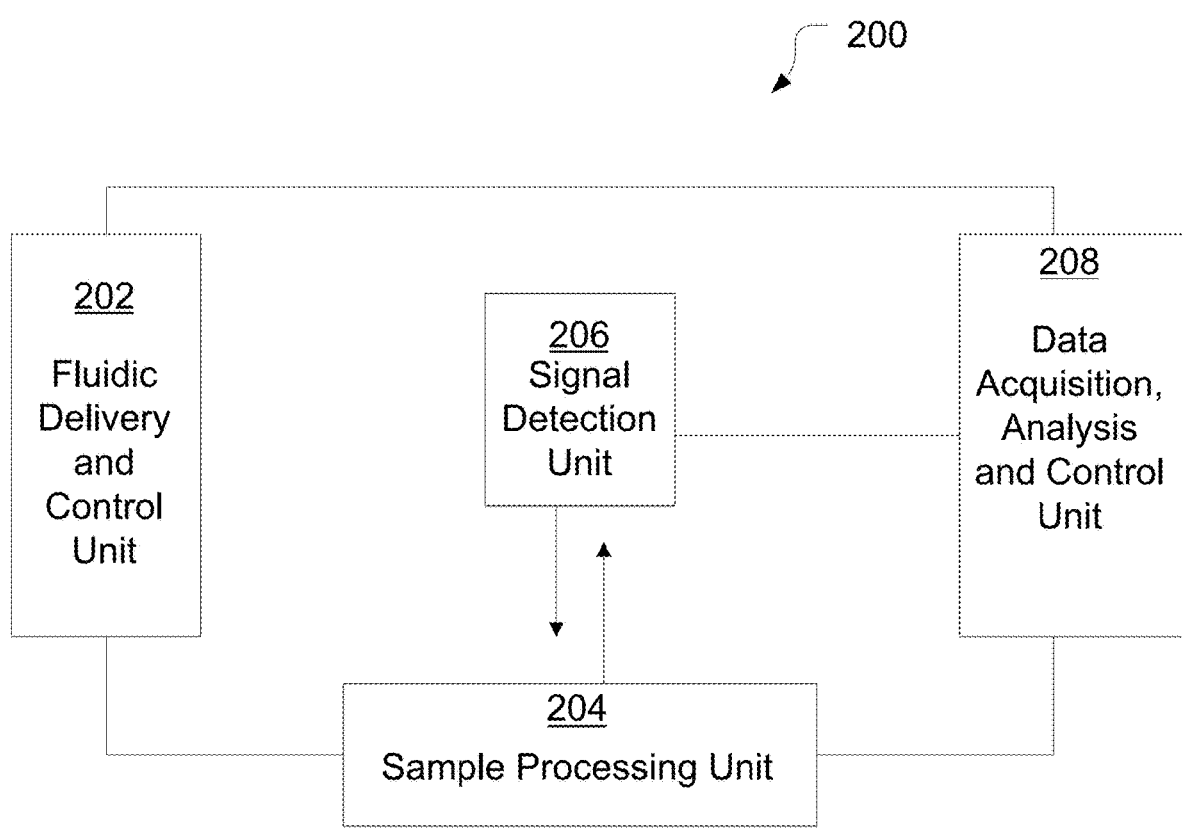
FIG. 2 is a schematic diagram of a system for reconstructing a nucleic acid sequence, in accordance with various embodiments.

Various embodiments of nucleic acid sequencing platforms, such as a nucleic acid sequencer, can include components as displayed in the block diagram of FIG. 2. According to various embodiments, sequencing instrument 200 can include a fluidic delivery and control unit 202, a sample processing unit 204, a signal detection unit 206, and a data acquisition, analysis and control unit 208. Various embodiments of instrumentation, reagents, libraries and methods used for next generation sequencing are described in U.S. Patent Application Publication No. 2009/0127589 and No. 2009/0026082 are incorporated herein by reference. Various embodiments of instrument 200 can provide for automated sequencing that can be used to gather sequence information from a plurality of sequences in parallel, such as substantially simultaneously.

In various embodiments, the fluidics delivery and control unit 202 can include reagent delivery system. The reagent delivery system can include a reagent reservoir for the storage of various reagents. The reagents can include RNA-based primers, forward/reverse DNA primers, oligonucleotide mixtures for ligation sequencing, nucleotide mixtures for sequencing-by-synthesis, optional ECC oligonucleotide mixtures, buffers, wash reagents, blocking reagent, stripping reagents, and the like. Additionally, the reagent delivery system can include a pipetting system or a continuous flow system which connects the sample processing unit with the reagent reservoir.

In various embodiments, the sample processing unit 204 can include a sample chamber, such as flow cell, a substrate, a micro-array, a multi-well tray, or the like. The sample processing unit 204 can include multiple lanes, multiple channels, multiple wells, or other means of processing multiple sample sets substantially simultaneously. Additionally, the sample processing unit can include multiple sample chambers to enable processing of multiple runs simultaneously. In particular embodiments, the system can perform signal detection on one sample chamber while substantially simultaneously processing another sample chamber. Additionally, the sample processing unit can include an automation system for moving or manipulating the sample chamber.

In various embodiments, the signal detection unit 206 can include an imaging or detection sensor. For example, the imaging or detection sensor can include a CCD, a CMOS, an ion sensor, such as an ion sensitive layer overlying a CMOS, a current detector, or the like. The signal detection unit 206 can include an excitation system to cause a probe, such as a fluorescent dye, to emit a signal. The expectation system can include an illumination source, such as arc lamp, a laser, a light emitting diode (LED), or the like. In particular embodiments, the signal detection unit 206 can include optics for the transmission of light from an illumination source to the sample or from the sample to the imaging or detection sensor. Alternatively, the signal detection unit 206 may not include an illumination source, such as for example, when a signal is produced spontaneously as a result of a sequencing reaction. For example, a signal can be produced by the interaction of a released moiety, such as a released ion interacting with an ion sensitive layer, or a pyrophosphate reacting with an enzyme or other catalyst to produce a chemiluminescent signal. In another example, changes in an electrical current can be detected as a nucleic acid passes through a nanopore without the need for an illumination source.

In various embodiments, data acquisition analysis and control unit 208 can monitor various system parameters. The system parameters can include temperature of various portions of instrument 200, such as sample processing unit or reagent reservoirs, volumes of various reagents, the status of various system subcomponents, such as a manipulator, a stepper motor, a pump, or the like, or any combination thereof.

It will be appreciated by one skilled in the art that various embodiments of instrument 200 can be used to practice variety of sequencing methods including ligation-based methods, sequencing by synthesis, single molecule methods, nanopore sequencing, and other sequencing techniques.

In various embodiments, the sequencing instrument 200 can determine the sequence of a nucleic acid, such as a polynucleotide or an oligonucleotide. The nucleic acid can include DNA or RNA, and can be single stranded, such as ssDNA and RNA, or double stranded, such as dsDNA or a RNA/cDNA pair. In various embodiments, the nucleic acid can include or be derived from a fragment library, a mate pair library, a ChIP fragment, or the like. In particular embodiments, the sequencing instrument 200 can obtain the sequence information from a single nucleic acid molecule or from a group of substantially identical nucleic acid molecules.

In various embodiments, sequencing instrument 200 can output nucleic acid sequencing read data in a variety of different output data file types/formats, including, but not limited to: *.fasta, *.csfasta, *seq.txt, *qseq.txt, *.fastq, *.sff, *prb.txt, *.sms, *srs and/or *.qv.

Genomic Variant Annotation System

Systems and methods for annotating biological information with functional and/or interpretive information are disclosed. The annotations can provide commentary or explanatory notes related to the biological information. The biological information can include sequence information, genomic variants (for example, SNPs, Indels, CNVs, inversions, etc.) identified from analyzing nucleic acid sequence data, and the like. That is, the various embodiments disclosed herein can utilize external sources of information (for example, annotation data sources and manually entered comments or information) to associate information that may be helpful in understanding or interpreting the consequences of biological information on cell function, disease progression, therapeutic efficacy, inherited traits, etc. The annotations can include information relating to intron-exon boundaries, regulatory sequences, repeats, gene names, and protein products that are relevant to the identified biological information, as well as relating the biological information to clinical and research results and outcomes.

Examples of annotation sources, include, but are not limited to gene transport format (GTF) database from RefGene database/NCBI (used to determine whether a variant overlaps a gene or exon), the dbSNP database/National Center for Biotechnology Information (NCBI) (contains information on SNPs and indels already found by other studies), Genome 10K, The Cancer Genome Atlas, etc. These annotations can be useful in helping to determine the potential functional consequences of the identified genomic variant.

Figure 3:
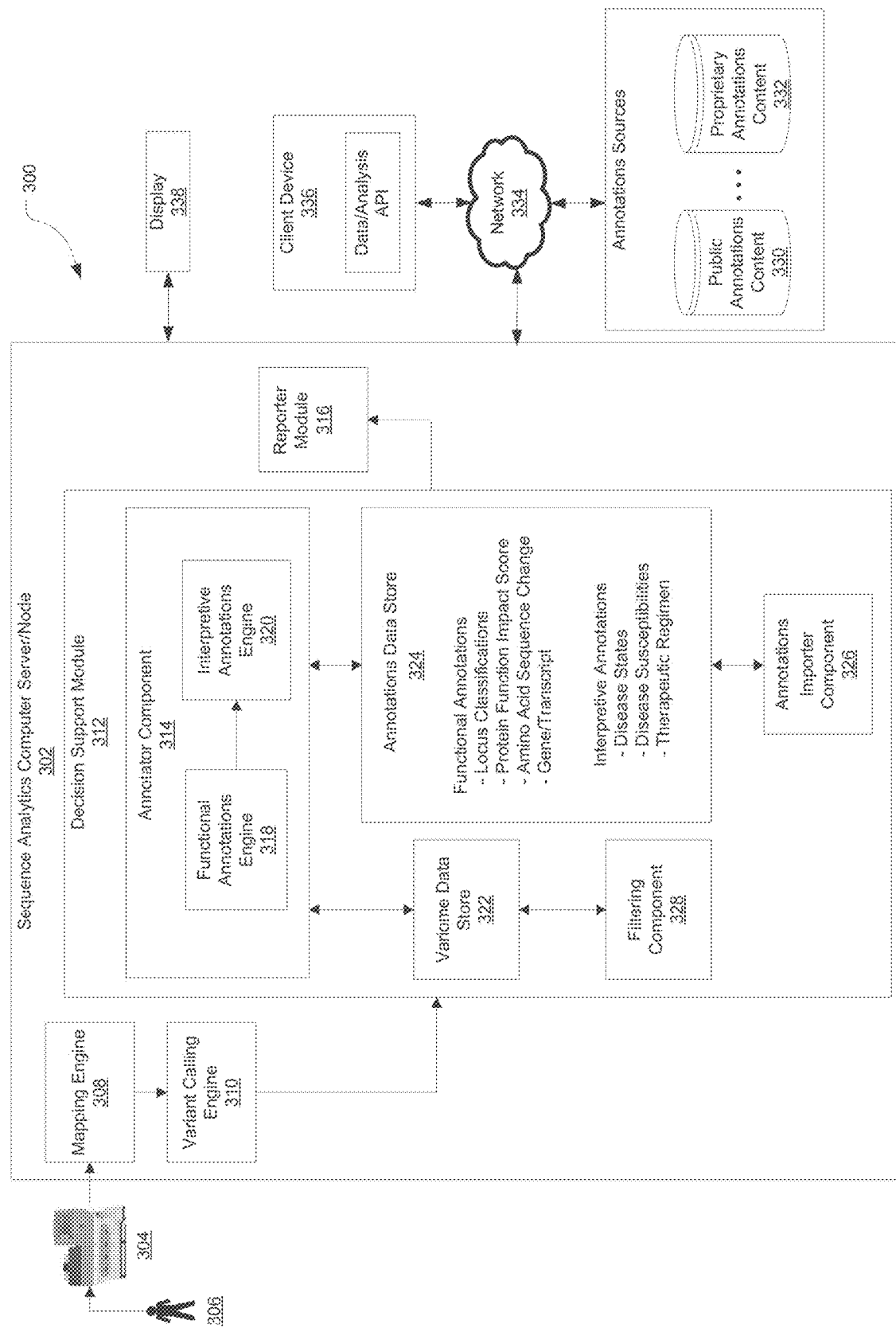
FIG. 3 is a schematic diagram of a system for annotating genomic variants, in accordance with various embodiments.

FIG. 3 is a schematic diagram of a system for annotating genomic variants, in accordance with various embodiments.

As depicted herein, annotation system 300 can include a nucleic acid sequence analysis device 304 (for example, nucleic acid sequencer, real-time/digital/quantitative PCR instrument, microarray scanner, etc.), an analytics computing server/node/device 302, a display 338 and/or a client device terminal 336, and one or more public 330 and proprietary 332 annotations content sources.

In various embodiments, the analytics computing server/node/device 302 can be communicatively connected to the nucleic acid sequence analysis device 304, client device terminal 336, public annotations content source 330 and/or proprietary annotations content source 332 via a network connection 334 that can be either a "hardwired" physical network connection (for example, Internet, LAN, WAN, VPN, etc.) or a wireless network connection (for example, Wi-Fi, WLAN, etc.).

In various embodiments, the analytics computing device/server/node 302 can be a workstation, mainframe computer, distributed computing node (part of a "cloud computing" or distributed networking system), personal computer, mobile device, etc. In various embodiments, the nucleic acid sequence analysis device 304 can be a nucleic acid sequencer, real-time/digital/quantitative PCR instrument, microarray scanner, etc. It should be understood, however, that the nucleic acid sequence analysis device 304 can essentially be any type of instrument that can generate nucleic acid sequence data from samples obtained from an individual 306.

The analytics computing server/node/device 302 can be configured to host a mapping engine 308, a variant calling engine 310, a decision support module 312 and a reporter module 316.

The mapping engine 308 can be configured to align or map a query nucleic acid sequence read to a reference sequence. Generally, the length of the sequence read is substantially less than the length of the reference sequence. In reference sequence mapping/alignment, sequence reads can be assembled against an existing backbone sequence (for example, reference sequence, etc.) to build a sequence that is similar but not necessarily identical to the backbone sequence. Once a backbone sequence is found for an organism, comparative sequencing or re-sequencing can be used to characterize the genetic diversity within the organism's species or between closely related species. In various embodiments, the reference sequence can be a whole/partial genome, whole/partial exome, whole/partial transcriptome, etc.

In various embodiments, the sequence read and reference sequence can be represented as a sequence of nucleotide base symbols in base space. In various embodiments, the sequence read and reference sequence can be represented as one or more color symbols in color space. In various embodiments, the sequence read and reference sequence can be represented as nucleotide base symbols with signal or numerical quantitation components in flow space.

In various embodiments, the alignment of the sequence read and reference sequence can include a limited number of mismatches between the bases that comprise the sequence read and the bases that comprise the reference sequence. Generally, at least a portion of the sequence read can be aligned to a portion of the reference sequence, such as a reference nuclear genome, a reference mitochondrial genome, a reference prokaryotic genome, a reference chloroplast genome, or the like, in order to minimize the number of mismatches between the sequence fragment and the reference sequence.

The variant calling engine 310 can be configured to receive mapped sequence reads from the mapping engine 308 and analyze the mapped reads to detect and call or identify one or more variants within the reads. Examples of variants that can be called by a variant calling engine 310 include but are not limited to: single nucleotide polymorphisms (SNP), nucleotide insertions or deletions (indels), copy number variations (CNV) identification, inversion polymorphisms, and the like. The variants changes to transcript or expression levels, etc. The variants can include mutations within a coding region that alter an expressed amino acid sequence, mutations that affect the rate of translation, maturation, or transport of a protein, mutations that affect mRNA splicing, mutations that affect the rate of transcription or the stability of an RNA, mutations that affect chromatin remodeling, or the like.

The reporter module 316 can be in communications with the decision support module 312 and be configured to generate a summary report of the called genomic variants that have been annotated by the annotator component 314 that can be part of the decision support module 312.

The decision support module can include an annotator component 314, a variome data store 322, an annotations data store 324, a filtering component 328 and/or an annotations importer component 326. In various embodiments, the annotator component 314 can be in communication with the variant calling engine 310, the variome data store 322 and/or the annotations data store 324. That is, the annotator component 314 can request and receive data and information (through, for example, data streams, data files, text files, etc.) from variant calling engine 310, variome data store 322 and annotations data store 324. In various embodiments, the variant calling engine 310 can be configured to communicate variants called for a sample genome in various formats, such as, but not limited to, variant call format (VCF), generic feature format (GFF) heirachical data format (HDF), genome variation format (GVF), or HL7 formatted data. It should be understood, however, that the called variants can be communicated using any file format where the called variant information can be parsed and/or extracted for later processing/analysis.

The variome data store 322 can be configured to store the variant calls received from the variant calling engine 310 and/or the annotator component 314 in a format that is accessible for mining.

That is, the called variant data can be maintained as a database or instantiated in some other persistent (and queryable) electronic form in the device memory (for example, hard drive, RAM, ROM, etc.) of the analytics computing server/node/device 302. The called variant data can be structured and use a common syntax and semantic model throughout or include appropriate interpreters between formats that allow for one-to-one mapping between terms and data types. In various embodiments, the variome data store 322 can be an indexed database table of variants. In particular embodiments, the indexed database can be configured for fast querying and filtering operations.

The annotations data store 324 can be in communications with the annotations importer component 326 and be configured to store data and information that can be used by the annotator component 314 to annotate the called variants. That is, the annotations data store 324 can store annotation data and information that can be relevant to the role that the called variant plays in the function, such as at a chromosome level, gene level, a transcript level, a protein level, or the like, (for example, functional type annotations) and/or the biological impact (for example, interpretive type annotations) of the called variants. In various embodiments, functional type annotations can include, but are not limited to: locus classification of the called variant, protein function impact score of the called variant, amino acid changes resulting from the called variant, gene/transcripts affected by the called variant, etc. In various embodiments, interpretive type annotations can include, but are not limited to: disease states or susceptibility to a disease (for example, cancer, diabetes, hypertension, heart disease, etc.) associated with the called variant, impacts that the called variant has on a particular therapeutic regimen (for example, drugs, surgical options, medical device, psychiatric therapy, lifestyle changes, drug sensitivities, etc.), presence of the variant on a list of annotated variants, etc. For example, a SNP variant call can be annotated with functional type annotations that point to the transcripts that the called SNP impacts and interpretive type annotations that are directed to diagnosing a particular disease state or a susceptibility to a disease.

The annotations importer component 326 can be configured to receive annotations content from one or more public 330 or proprietary 332 annotations content sources and convert the annotations content into a format that can be stored in the annotations data store 324 and is accessible for mining. That is, the annotations importer component 326 can convert annotations data and/or information into a format that can be stored onto a database or instantiated in some other persistent (and queryable) electronic form in the device memory (for example, hard drive, RAM, ROM, etc.) of the analytics computing server/node/device 302.

In various embodiments, annotations content can be manually entered or uploaded by a user to the annotations importer component 326 via a computer readable storage medium that is communicatively connected (for example, via a serial data bus connection, parallel data bus connection, internet/intranet network connection, etc.) to the analytics computing server/node/device 302. That is, a user can selectively upload annotations content to the annotations data store 324 depending on the requirements of the particular application. Examples of computer readable medium include, but are not limited to: hard drives, network attached storage (NAS), read-only memory, random-access memory, CD-ROMs, CD-Rs, CD-RWs, magnetic tapes, FLASH memory and other optical/non-optical data storage devices.

In various embodiments, annotations content can be automatically requested and sent from public 330 and/or proprietary 332 annotations content sources to the annotations importer component 326 through the use of a data refresh executable or script. That is, the annotations content in the annotations data store 324 can be continuously refreshed as the public 330 and/or proprietary 332 annotations content sources are updated with new or modified annotations content.

In various embodiments, the annotator component 314 can include a functional annotations engine 318 and interpretive annotations engine 320.

The functional annotations engine 318 can be configured to receive called variants from the variome data store 322, associate one or more functional type annotations (stored in the annotations data store 324) to the called variants and update the called variant records in the variome data store 322 with the associated functional type annotations. In various embodiments, the functional annotations engine 318 can be configured to annotate all called variants that fall within a block of overlapping transcripts (in the sample genome) at the same time. That is, the functional annotations engine 318 can group overlapping transcripts together into a "gene block" and then annotate all variants in the gene block together. The advantage here is that all called variants that are potentially mutually interacting can be grouped and annotated together to give researchers/clinicians greater insight into the synergistic or antagonistic interplay between variants.

In various embodiments, the functional annotations engine 318 can be selectively configured to annotate only called variants that fall within a coding region (for example, exons, codons) of the sample genome being annotated. In various embodiments, the functional annotations engine 318 can be selectively configured to annotate only called variants that fall within an intragenic region, such as an intron, of the sample genome being annotated. In various embodiments, the functional annotations engine 318 can be selectively configured to annotate only the called variants in the intergenic region of the sample genome being annotated.

In various embodiments, the functional annotations engine 318 can receive the called variants in the form of a called variant data file (for example, *.vcf or other file format), associate the functional type annotations, and store the variants and annotations to the variome data store 322. In various embodiments, the functional annotations engine 318 can receive the called variants as variant data (for example, variant base identity and genome position, etc.), associates one or more functional type annotations to the called variant and directly updates the called variant record in the variome data store 322 with the associated functional type annotations information. That is, the functional annotations engine 318 can receive called variants directly from the variome data store 322, annotate them and save them back on the variome data store 322 or alternate data store.

Figure 4:
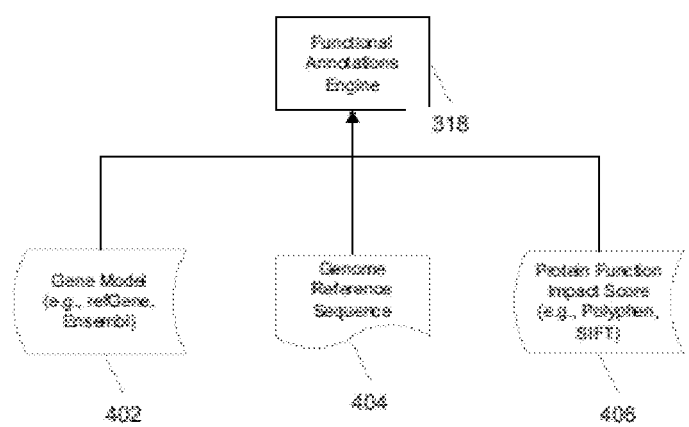
FIG. 4 is a depiction of the different kinds of functional type annotations information that the functional annotations can annotate called variants with, in accordance with various embodiments.

As shown in FIG. 4, the functional annotations engine 318 can annotate the called variants with several different kinds of functional type annotations information. In various embodiments, the functional annotations engine 318 can be configured to first annotate the called variants with information, such as which transcripts they are associated with using "gene model" information 402 from one or more public or proprietary sources (for example, refGene, Ensembl, etc.). That is, applying gene transcript information from a "gene model" to the called variant to provide information about which transcripts that the called variant is found in (or impacts). Typically, the gene model selected is from the same species as the organism that supplied the sample genome that is being analyzed. It should be understood, however, that in certain applications it may be instructive to a researcher or clinician to annotate called variants against the gene models of other species.

In various embodiments, the functional annotations can also be configured to map the coding regions, such as exons, of the transcripts which are associated with each called variant to a reference genome 404 to obtain base information about the codons. That is, the base sequence information provided by the reference genome can be used to fill in the base information for the actual codons where the called variants are found and/or in the transcripts the called variant are found.

In various embodiments, the functional annotations engine 318 can be configured to associate a protein function impact score 406 to each called variant using one or more public or proprietary modeling tools/algorithms (for example, POLYPHEN, SIFT, Grantham, GERP, etc.). The scores can predict the likelihood that a called variant which causes an amino acid substitution will have a deleterious effect on the structure and function of a human protein.

The interpretive annotations engine 320 can be configured to receive called variants from the variome data store 322, associate one or more interpretive type annotations (stored in the annotations data store 324) to the called variants and update the called variant records in the variome data store 322 with the associated interpretive type annotations.

In various embodiments, the interpretive annotations engine 320 receives the called variants in the form of a called variant data file (for example, *.vcf or other file format), associate the interpretive type annotations, and store the variants and annotations to the variome data store 322. In various embodiments, the interpretive annotations engine 318 receives the called variants as variant data (for example, variant base identity and genome position, etc.), associates one or more interpretive type annotations to the called variant and directly updates the called variant record in the variome data store 322 with the associated interpretive type annotations information.

In various embodiments, the interpretive annotations engine 320 can be selectively configured to annotate called variants in the sample genome being annotated. In various embodiments, the interpretive annotations engine 320 can be selectively configured to annotate called variants that fall within a coding region (for example, exons, codons) of the sample genome being annotated. In various embodiments, the interpretive annotations engine 320 can be selectively configured to annotate called variants that fall within an intragenic region, such as an intron, of the sample genome being annotated. In various embodiments, the interpretive annotations engine 320 can be selectively configured to annotate the called variants in the intergenic region of the sample genome being annotated.

In various embodiments, annotator component 314 can provide the variants to a third party annotation source, such as Public Annotations Content 330 or Proprietary Annotations Content 332 for annotation or interpretation. The third party annotation source can provide functional or interpretive annotations back to annotator component 314, and the annotations can be stored within Variome Data Store 322.

In various embodiments, the system can be configured to automate the processing of sample data. For example, a workflow can be selected to define how the data is processed by the mapping engine 308, the variant calling engine 310, and the annotator component 314. In particular embodiments, a workflow can be selected when setting up the run on the nucleic acid sequence analysis device 304 and the data can be automatically uploaded to the analytics computing device 302. Additionally, the workflow can be automatically launched when the data has been uploaded. In other embodiments, the data can be uploaded, manually or automatically, from the nucleic acid sequence analysis device 304 and the workflow can be selected and launched manually. Generally, once the workflow has been selected and launched, analysis can proceed from through the mapping engine 308, the variant calling engine, 310, and the annotator component 314 without further intervention by a user.

The filtering component 328 can be configured to allow a user to set filter conditions to filter out the called variants that are included in the summary report generated by the reporter module 316. Examples of filter conditions include, but are not limited to, filtering for: variants that are non-synonymous and fall within a particular gene, variants that are associated with a particular disease condition, variants that have a functional score of greater or less than a selected value, novel variants that are not present in a functional type annotations source, variants that fall in gene panel regions (defined by user), etc. In various embodiments, the filtering component 328 can utilize combinations of filters, such as for example filtering for variants that fall within a particular gene and have a functional score indicative of a significant effect.

In various embodiments, the filtering component 328 can be configured with a collection of filters to select for variants with a high likelihood of having possible functional significance. For example, the filtering component 328 can select for missense mutations and nonsense mutations and exclude synonymous mutations. Additionally, the filtering component 328 can select for novel variants or clinically significant variants and exclude variants that have been identified to have limited functional or clinical significance. Novel variants can include variants that are not included in the annotations data store, variants that have not previously been classified as to their clinical or functional significance, or the like. Further, the filtering component 328 can select for variants that have a significant effect on the structure or stability of a protein and exclude variants that have a minimal effect on the protein, such as based on, for example, a function SIFT score. Still further, the filtering component 328 can select for variants that affect allele frequency. Also, the filtering component 328 may select or exclude variants at positions of known significance, such as positions known to have a high incidence of mutation in cancers, positions with a low or high number of false positive variant calls, positions known to have a minimal functional impact, or the like.

In various embodiments, the variome data 322 and the annotations data 324 stores can be combined into a single data store configured to store both called variant data and variant annotations information.

Client terminal 336 can be a thin client or thick client computing device. In various embodiments, client terminal 336 can have a web browser (for example, INTERNET EXPLORER™, FIREFOX™, SAFARI™, etc) that can be used to communicate information to and/or control the operation of the mapping engine 308, variant calling engine 310, decision support module 312, annotator component 314, filtering component 328, annotations importer component 326, variome data store 322, annotations data store 324, functional annotations engine 318 and/or interpretive annotations engine 320 using a browser to control their function. For example, the client terminal 336 can be used to configure the operating parameters (for example, match scoring parameters, annotations parameters, filtering parameters, data security and retention parameters, etc.) of the various modules, depending on the requirements of the particular application. Similarly, client terminal 336 can also be configured to display the results of the analysis performed by the decision support module 312 and the nucleic acid sequencer 304.

It should be understood that the various data stores disclosed as part of system 300 can represent hardware-based storage devices (for example, hard drive, flash memory, RAM, ROM, network attached storage, etc.) or instantiations of a database stored on a standalone or networked computing device(s).

It should also be appreciated that the various data stores and modules/engines shown as being part of the system 300 can be combined or collapsed into a single module/engine/data store, depending on the requirements of the particular application or system architecture. Moreover, in various embodiments, the system 300 can comprise additional modules, engines, components or data stores as needed by the particular application or system architecture or to extend functionality.

In various embodiments, the system 300 can be configured to process the nucleic acid reads in color space. In various embodiments, system 300 can be configured to process the nucleic acid reads in base space. In various embodiments, system 300 can be configured to process the nucleic acid sequence reads in flow space. It should be understood, however, that the system 300 disclosed herein can process or analyze nucleic acid sequence data in any schema or format as long as the schema or format can convey the base identity and position (or position range) of the nucleic acid sequence within the reference sequence.

In various embodiments, the system 300 can be configured to distinguish between positions with a called variant, positions that have been called as reference, and positions with no call. Positions with a called variant can include positions where sufficient evidence was provided by the reads to indicate the specimen sequence contains a variant. Positions that have been called as reference can include positions where there is sufficient evidence to support the conclusion that the specimen sequence is substantially identical to the reference sequence at the position. Positions with no call can include positions where there is insufficient evidence to determine if the specimen sequence is the same as or different from the reference sequence. For example, positions with no call can include positions with low coverage, positions with low base quality, or positions where the read sequences indicate different bases with insufficient homogeneity to determine the sequence with sufficient confidence. Generally, positions with no call can be indicated as matching the reference sequence and may be excluded from reporting of variants. However, for positions where the reference sequence has particular functional or clinical significance, a no call may be indicated on the report. For example, if a treatment has been found effective for individuals matching the reference sequence at a particular position but is contraindicated for individuals with certain variants at the position, a no call at the position can be indicated in a report. Thus, a clinician reviewing the report may determine that the treatment should be avoided without further evidence rather than relying on an indication that the position matches the reference sequence simply because no variant was identified.

Figure 5:
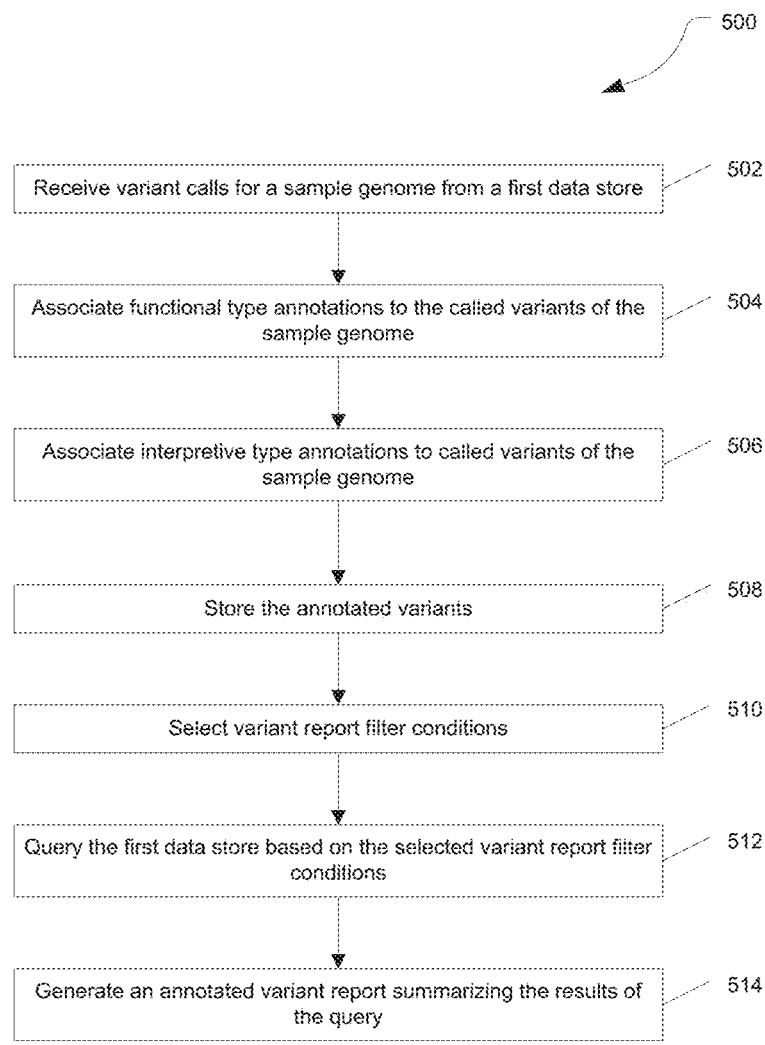
FIG. 5 is an exemplary flowchart showing a method for annotating genomic variants, in accordance with various embodiments.

FIG. 5 is an exemplary flowchart showing a method 500 for annotating genomic variants, in accordance with various embodiments.

In step 502, one or more variant calls for a sample genome are received from a first data source, such as a variome data source. In various embodiments, the variome data store can be configured to store the variant calls received from the variant calling engine in a format that is accessible for mining.

In step 504, functional type annotations are associated to called variants that fall within a block of overlapping transcripts (of the sample genome) at the same time, wherein the functional type annotations are stored in a second data store such as an annotations data store. That is, overlapping transcripts are grouped together into a "gene block" and then all the called variants in the gene block are annotated together. The advantage here is that multiple called variants that are potentially mutually interacting can be grouped and annotated together to give researchers/clinicians greater insight into the synergistic or antagonistic interplay between variants.

In various embodiments, only called variants that fall within an intragenic region or intron, of the sample genome are annotated. In various embodiments, only the called variants in the intergenic region of the sample genome are annotated.

In step 506, interpretive type annotations are associated to all called variants of the sample genome, wherein the interpretive type annotations are stored in a second data store, such as an annotations data store. In various embodiments, only called variants that fall within a coding region (for example, exons, codons) of the sample genome are annotated with the interpretive type annotations. In various embodiments, only called variants that fall within an intragenic region or intron of the sample genome are annotated. In various embodiments, only the called variants in the intergenic region of the sample genome are annotated.

In step 508, the annotated called variants are stored in the first data store, such as a variome data store. In various embodiments, called variants are stored after each annotation step. That is, the called variants are stored after being functionally annotated and stored again after the interpretive annotation step.

In step 510, variant report filter conditions are set by a user. These are filter conditions that users set to filter out the called variants that are included in the called variants summary report that is generated in a subsequent step. Examples of filter conditions include, but are not limited to, filtering only for: variants that are non-synonymous and fall within a particular gene, variants that are associated with a particular disease condition, variants that have a functional SIFT score of greater or less than a selected value, variants that are not present in dbSNP, variants that fall in gene panel regions (defined by user), etc, or combinations thereof.

In various embodiments, the samples, workflows, analyses, annotated variants, variant knowledge bases, and the like can be shared with other users through a collaboration space. A collaboration space enables the sharing of data with users outside of an organization, collaboration on workflow development and data analysis, and external review of a workflow or analysis. For example, cross organization research can use collaboration space to share data between researchers at different organizations. In another example, users can use a collaboration space to work with support personnel to define workflows, refine parameters used for various parts of the workflow, review results to diagnose software errors, add additional annotation data sets, and the like. In yet another example, results of an analysis can be shared with an external expert using a collaboration space to get a second opinion or additional insight as to a set of variants that a user is not familiar with.

In step 512, the first data store, such as a variome data store, is queried based on the selected variant report filter conditions.

In step 514, an annotated variant report is generated summarizing the results of the query in step 512. In various embodiments, the annotated variant report can be associated with de-identified personal information. The de-identified personal information may enable a clinician treating a patient to associate the report with the patient. However, the de-identified personal information may be insufficient on its own to associate the report with an individual.

Figure 6:
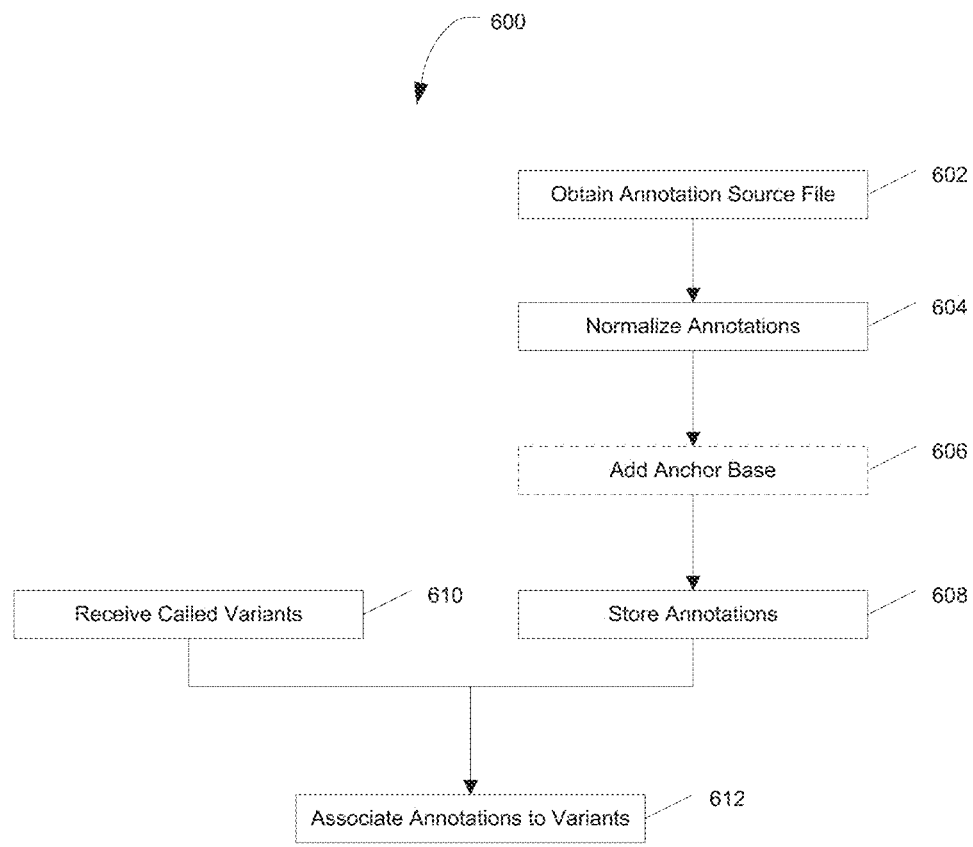
FIG. 6 is an exemplary flowchart showing a method for annotating genomic variants, in accordance with various embodiments.

FIG. 6 is an exemplary flowchart showing a method 600 for annotating genomic variants, in accordance with various embodiments.

In step 602, the annotation source file can be obtained. The annotation source file can include a list of genomic coordinates identifying the location within the genome corresponding to the annotation.

In step 604, the annotations can be normalized such that the genomic coordinates reference the same strand of the reference genome, such as the positive (+) strand.

In 606, an optional anchor base can be added. The anchor base can signify a normalized position, such as a left most or 5' position on the positive (+) strand, to which the variant can be assigned. For example, if the reference sequence contained ATATATAT and a variant sequence has been identified containing ATATAT, the variant could be annotated as either a TA deletion or an AT deletion. Furthermore, the annotation may be mapped to many positions within the repeated sequence. As such, an anchor base can be added to the annotation file to indicate the left most or 5' position of the repeated sequence. In various embodiments, the original position of the source annotation can also be maintained for future reference. In other embodiments, the anchor base can be at the right most or 3' position of the positive (+) strand.

Importantly, the genomic coordinate of the anchor base needs to be consistent for both forward (positive (+) strand) and reverse (negative (−) strand) reads.

In various embodiments, using left most or right most genome coordinates can cause problems when analyzing the results in translation space. Specifically, in translation space, the relevant affect is the change in amino acid sequence, which occurs at the 3' end of the coding strand. In particular embodiments, when working in translation space, the genomic coordinates can be converted to the 3' end of the coding strand as needed.

In step 608, the annotations can be stored in an annotations database.

In step 610, a set of called variants can be provided. The called variants can be assigned positions consistent with the normalized genomic coordinates of the annotations. For example, the called variants can be assigned left most or 5' positions on the positive (+) strand of the reference genome.

In step 612, annotations from the annotations database can be associated with the called variants, such as by matching the genomic coordinates of the called variants with the genomic coordinates of the annotations. In various embodiments, when the user is provided with the annotations associated with the called variants, such as in a report, the original position of the source annotation can be provided along with the anchor position.

As discussed above, conventional nucleic acid sequence analysis systems do not lend themselves to easy analysis and interpretation of genomic variant candidates identified in nucleic acid sequencing data. A step towards rectifying this shortfall is the development of new user interfaces and methods for graphically displaying and configuring nucleic acid sequence data analysis workflows/pipelines in a clear and effective manner to allow a researcher/clinician to readily navigate through the myriad of data analysis options and configurations.

In various embodiments, various functions required for analyzing specimen data can be provided. For example, these functions can include importing the data, configuring workflows, analyzing specimen data using a configured workflow, reviewing the results, interpreting the biological significance of the identified variants, and producing reports. Additionally, multiple roles can be defined. Roles can be assigned one or more functions, and functions can be restricted to specific roles. For example, an import role, a analyze role, and a report role can be defined. The import role can be assigned the functions of importing sample data and performing pre-configured workflows, the analyze role can be assigned the functions of configuring a workflow and reviewing the results, and the report role can be assigned the functions of interpreting the biological significance and producing reports. In particular embodiments, multiple roles can be assigned the same functions. For example, both the analyze role and the import role can be assigned the tasks of importing and performing pre-configured workflows, while the functions of configuring a workflow and reviewing the results can be restricted to the analyze role. In particular embodiments, a user can define custom roles and assign functions to the custom roles. Additionally, the roles can be assigned to users such that an individual user can be provided with the capability to perform certain functions and may not have access to other functions.

Figure 7:
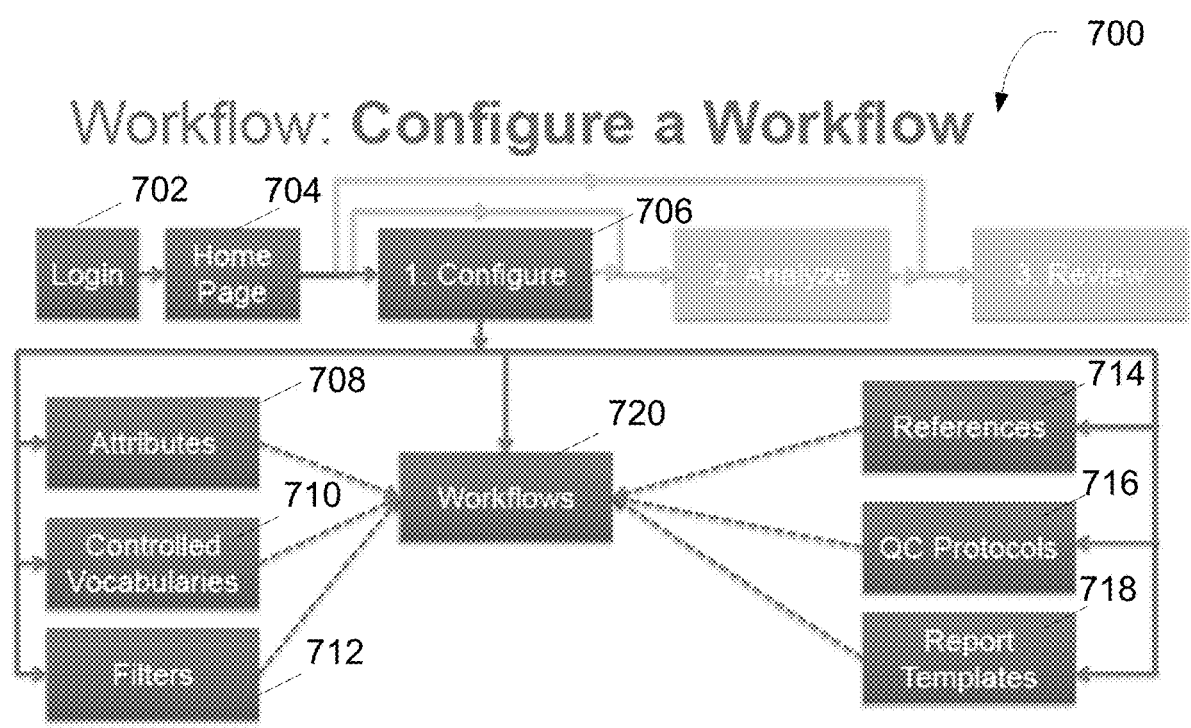
FIG. 7 is an exemplary flowchart showing a method for configuring a workflow, in accordance with various embodiments.

FIG. 7 is an exemplary flow diagram 700 illustrating a configuring a workflow function. At 702, a user can be presented with a login screen. Logins can be based on individual accounts, to which specific roles have been granted. For example, by logging in to an account that has been granted the analyze role, access to the function of configuring a workflow can be provided.

At 704, the user can be presented with a home page. The home page can present the user with links to the functions available to the user, such as access to configure a workflow.

At 706, the user can be presented with an interface for configuring a workflow. Completion of the configuration can be dependent on completion of several sub-functions, such as configuring Attributes, Vocabularies, Filters, Annotation Sets, QC Protocols, and Report Templates. Through the configure interface, a user can access the sub-functions required to configure the workflow. All of these sub-functions can follow a Create→Save→Publish paradigm to create a new object, save it for review, and publish it for use by others when it is finalized. The publishing function in particular can require authority of an individual within the analyze role. The inputs allowed in the Configurations tab, can include but are not limited to: search/advanced search functions to allow a keyword to be used to find a specific report template, checkboxes for activation or inactivation of those items that are not finalized (published) and are still available to be viewed, edited, or cloned to develop a new item, a button to allow for the creation of a new item, etc.

Figure 8:
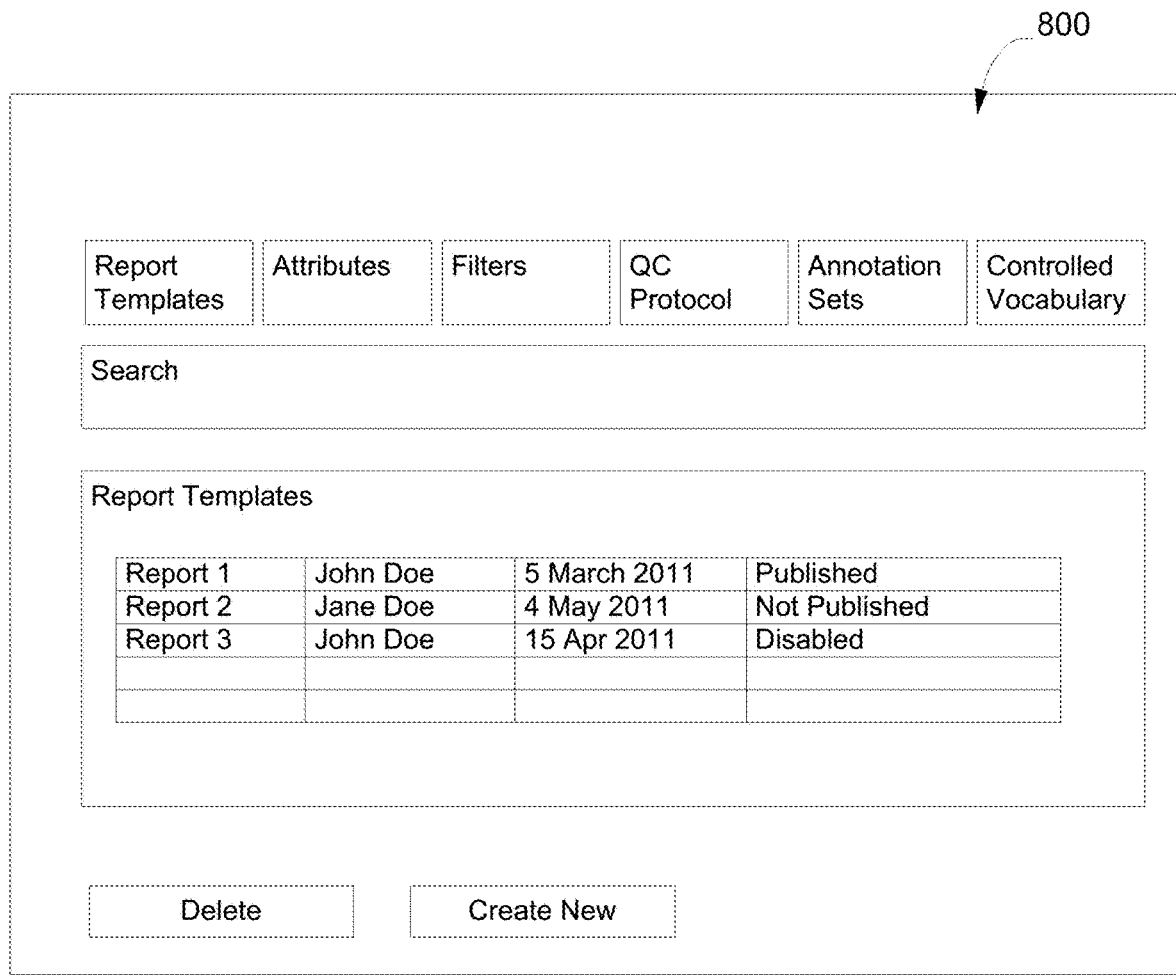
FIG. 8 is a diagram showing an exemplary interface for configuring a workflow, in accordance with various embodiments.

FIG. 8 provides an exemplary interface 800 for configuring a workflow. It can allow direct navigation to the 6 sub-functions (for example, attributes, controlled vocabularies, filters, annotation sets, QC templates, report templates) that should be completed before the main function—configuring a workflow—is possible.

At 708, the user can be presented with an interface for configuring attributes that can be used elsewhere throughout the system. An attribute can define a consistent place to store structured metadata about a specific object (for example, sample) in the system, such as Library, Library Type, Sample, Barcode (Index), File Path, etc. Additionally, attributes can be used to define relation between samples (tumor, normal, mother, father, offspring), connections between a set of relations (such as, paired for tumor/normal or trio for mother/father/offspring), and specimen types to describe the tissue source (blood, FFPE, fresh, etc).

At 710, the user can be presented with an interface for configuring controlled vocabularies. Controlled vocabularies can normalize the usage of semantic concepts within the system and can facilitate mapping to external nomenclature sets. In its simplest form, this can allow normalization across spelling, capitalization, word order, etc. Additionally, relating internal concepts to external nomenclatures such as HUGO gene names, disease or drug lists, or pathogenicity of a variant can allow them to be harmonized more easily.

At 712, the user can be presented with an interface for configuring filters. The filters can be used to refine the variant list for review. The filters can focus on specific aspects of the variant calls, such as their functional properties (for example, non-synonymous) or their relative allele frequency within the sample.

At 714, the user can be presented with an interface for configuring reference genome assemblies. The interface can show the reference genome assemblies that have been loaded into the system and can allow the creation (importing) of new reference assemblies. Creating a new reference assembly can include importing a sequence file and configuring genomic annotations to be used with the sequence file. The genomic annotations can be uploaded or selected from a preexisting annotations source, such as dbSNP (list of known SNPs from dbSNP at NCBI), COSMIC (associations between variants and cancers in the COSMIC database), OMIM (Associations between variants and Mendelian traits from OMIM/NCBI), Genemodel (the description of a single gene), Geneset (a set of multiple genes throughout the genome) and VariantKB (the internal variant knowledge base).

Figure 9:
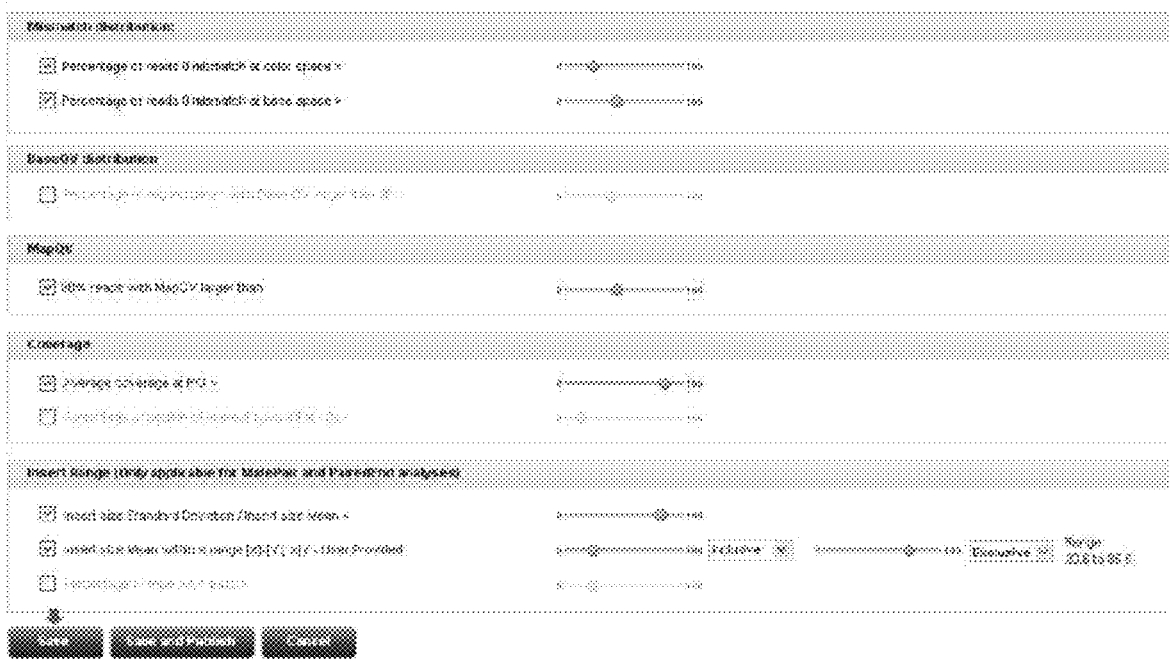
FIG. 9 is a diagram showing an exemplary interface for configuring a quality control protocol, in accordance with various embodiments.

At 716, the user can be presented with an interface for configuring QC Protocols. QC Protocols can be used to assess performance of an individual specimen analysis. QC Protocols can describe the requirements for success by defining thresholds for each metric to be used in assessing run quality—sequencing depth, GC bias, strand bias, etc.— and thus the validity of the variant calls derived within that analysis. The selected criteria can be calculated from the relevant set of input reads (such as, FASTQ, CSFASTQ, or SFF), mapped reads (such as, SAM or BAM), variants (such as VCF) or at other related steps in the processing. The interface can include a set of previously defined metrics and allow for the inclusion/exclusions of individual metrics and setting of tolerance thresholds for each metrics. FIG. 9 illustrates an exemplary interface 900 for configuring a QC Protocol.

At 718, the user can be presented with an interface for configuring report templates. Report templates can allow the customization of the report structure and describe the way data is to be presented. For example, the report template can define where information, such as specimen details, report type, and results, is presented in the report.

At 720, the user can be presented with an interface for configuring workflows. Workflows can describe a set of modules (for example, read QC metrics, read mapping, SNP detection) to be included and configured for a new test within the system. The basic steps to generate a new workflow are: 1. creation of Workflow Details—the high level description of the workflow, 2. customization of modules—describing which modules will be run and configuring their input parameters, 3. selection of a QC template to certify that the data were generated properly before variant calling, and 4. selection of a Report Template to format the variant results for messaging outside the lab.

Once the workflow is configured and published, it can be run on specimen samples by a user assigned the Import role or the Analyze role. When the results are ready, they are analyzed and reviewed a user with the Analyze role.

Figure 10:
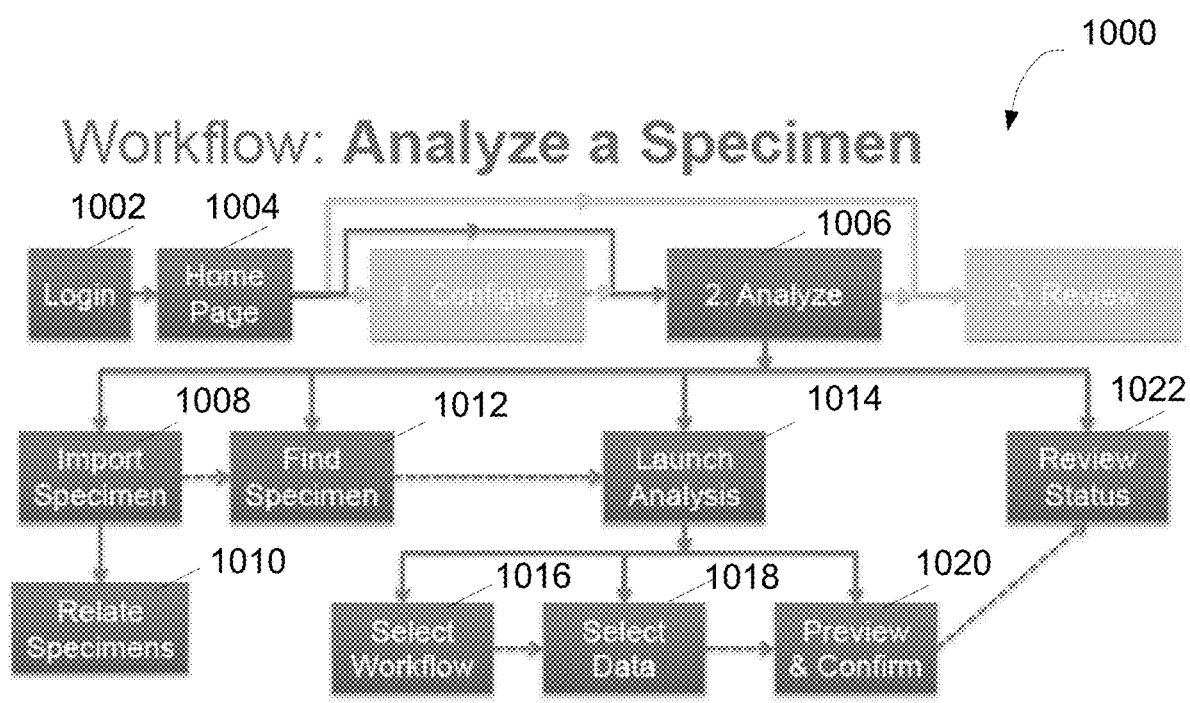
FIG. 10 is an exemplary flowchart showing a method for analyzing a specimen, in accordance with various embodiments.

FIG. 10 is an exemplary flow diagram 1000 illustrating the 'analyze a specimen' function. At 1002, a user can be presented with a login screen. Logins can be based on individual accounts, to which specific roles have been granted. For example, by logging in to an account that has been granted the analyze role or the import role, access to the function of analyzing a specimen can be provided.

At 1004, the user can be presented with a home page. The home page can present the user with links to the functions available to the user, such as access to analyze a specimen.

At 1006, the user can be presented with an interface for analyzing a specimen. The interface can direct the user to select a workflow, select data (specimen), preview and confirm, and then to launch the analysis.

At 1008, the user can be presented with an interface for importing a specimen. Importing a specimen can involve specifying the metadata (specimen information) and the data itself (sequence data) that is derived from that specimen. The metadata can be uploaded from a text file in a specific format, and the sequence data file may be specified with the metadata or may be uploaded separately.

At 1010, the user can be presented with an interface for relating specimens. Relating specimens can allow the aggregation of multiple specimens to be used in a single analysis and can allow their relative roles to be defined. For example, a trio relation can have three specimens that are defined to be from the mother, father, and offspring (perhaps self or proband). In various embodiments, more complex pedigrees can be constructed by connecting multiple trio relations together through an individual, such as having the individual as an offspring in one trio and a parent in one or more other trios. In another example, a paired relation can have two specimens that are defined to be from normal tissue and a tumor.

At 1012, the user can be presented with an interface for selecting one or more specimens for analysis. The interface can include a search function, an advanced search function, a list of available specimens, or other functionality to assist the user in finding and selecting the specimen for analysis. Additionally, for related specimens, the interface can provide a way to identify related specimens or can automatically select related specimens when a first specimen of the relation is selected.

At 1014, the user can be presented with an interface for launching an analysis. The interface can guide the user through multiple sub-functions for preparing and initiating the analysis. At 1016, the user can be presented with an interface for selecting a workflow. For example, the interface may provide a list of workflows and the user can select a workflow by clicking on the workflow or a checkbox associated with the workflow. At 1018, the user can be presented with an interface for selecting the data for analysis. For example, the interface may provide a list of specimens or data files associated with selected specimens that are available for analysis with the selected workflow. In particular embodiments, the list of specimens or data files can be filtered to present only specimens or data files appropriate for the selected workflow. For example, if a paired analysis workflow is selected, the list of specimens or data files may be limited to those specimens that have been identified as part of a paired relation. Another example is that reads can be required for workflows containing a mapping component as the data type should be compatible with the workflow; if input data is VCF (variants), this is not appropriate for a mapping workflow. At 1020, the user can be presented with an interface for previewing and confirming the selected analysis.

At 1022, the user can be presented with an interface for reviewing the status of analyses. The interface can display the status of currently running analyses and identify analyses that successfully completed or that failed, such as by failing the associated QC Protocol. Additionally, the interface can identify analyses that have been queued but have not yet launched.

Figure 11:
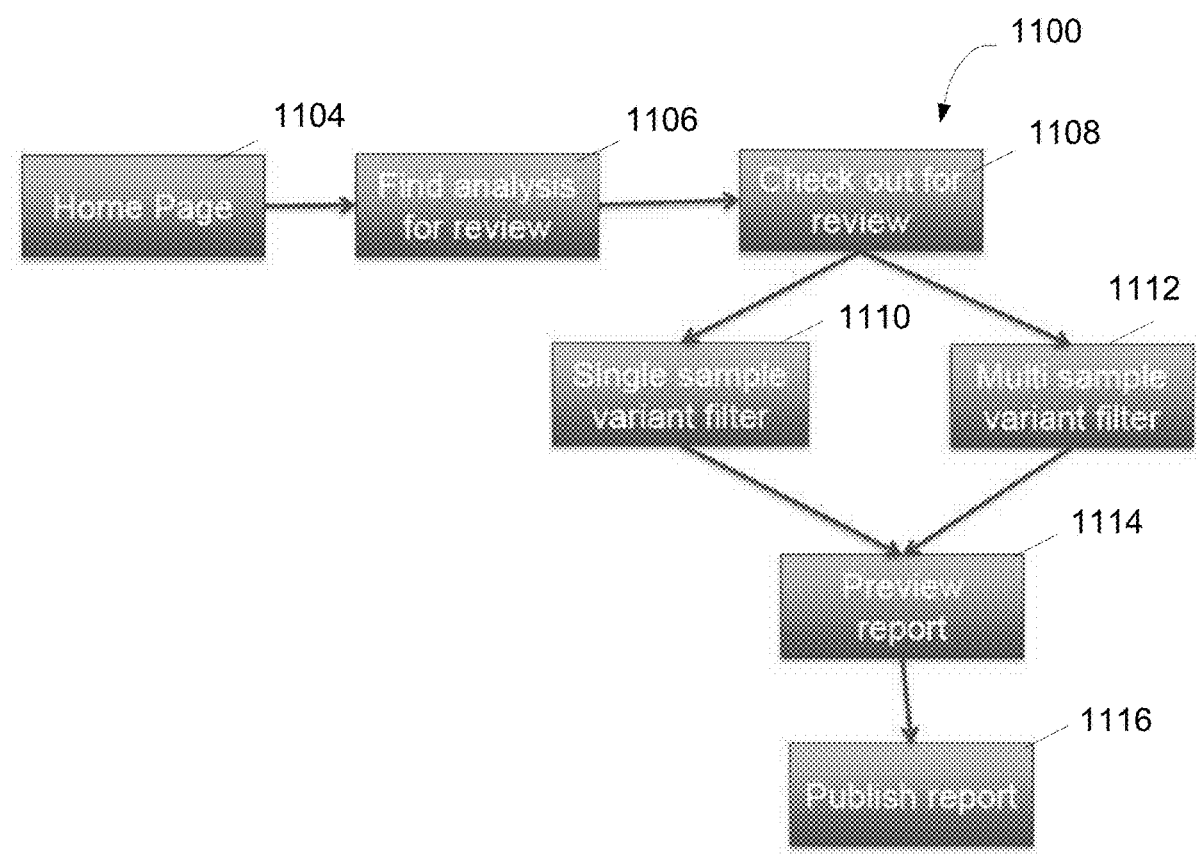
FIG. 11 is an exemplary flowchart showing a method for publishing a report, in accordance with various embodiments.

FIG. 11 is an exemplary flow diagram 1100 illustrating the 'publish a report' function. A user can be presented with a login screen. Logins can be based on individual accounts, to which specific roles have been granted. For example, by logging in to an account that has been granted the report role, access to the function of publish a report can be provided.

At 1104, the user can be presented with a home page. The home page can present the user with links to the functions available to the user, such as access to publish a report. The 'publish a report' function can direct the user to select an analysis (specimen), review and filter variants and annotations, and then to publish the report.

At 1106, the user can be presented with an interface for finding an analysis for review. The interface can provide a search function, an advanced search function, a list of analyses available for review, or other functionality to enable the user to find and select an analysis for review. In various embodiments, the interface can provide a list of samples for which the annotation is complete and are available for preparing a report. Additionally, the interface can provide an indication of which stage the report is in. For example, clicking on a plus sign by the sample name can expand the list to provide the stage of individual analysis. Stages that are greyed out are may not completed. The current stage can be the last ungreyed stage in the list.

At 1108, the user can check out the analysis for review. By checking out the analysis, the system can limit the ability of multiple users from working on the same analysis or report.

At 1110, the user can select single sample variant filters. Single sample variant filters can be applied to select, for example, variants that have a higher likelihood of being clinically significant. The variants may be filtered by disease, gene panel, variant type, database, values of functional predictions, etc.

At 1112, the user can select multi sample variant filters. Multi sample variant filters can be applied to, for example, a paired analysis, such as with Tumor/Normal pairs, or a Trio, such as a set of Mother/Father/Child. Tumor/Normal pairs typically represent specimens from two different tissues within a single individual. The normal is a somewhat 'matched' control—best if it is a specimen from the ipsilateral tissue (other side of the body), but this may vary with access to 'normal' tissue. Trios are sets of Mother/Father/Child specimens, usually germline, that are used to detect de novo mutations (present only in the child) or Mendelian Inheritance inconsistencies. Multi sample variant filters can be used to select variants that are common to more than one specimen, or variants that are unique to a single specimen of the group. For example, a paired analysis can be filtered to select variants that are unique to tumor tissue.

In various embodiments, paired analysis can provide an indication of which variants are unique to a tumor sample and which variants are common to the tumor sample and a normal control sample. Identifying variants unique to the tumor sample can aid in identifying therapies that are effective against the tumor. Additionally, identifying variants common to the tumor and the normal control sample, or variants that are unique to the control sample, can aid in identifying therapies that minimize side effects for a patient. Alternatively, in a research setting, identifying variants that are unique to the tumor can provide insight on tumor progression and mechanisms for cancer development.

In various embodiments, and interface showing a Venn diagram displaying the variants that are common or are shared between the three members of a trio (mother/father/child) or a paired sample (Tumor/Normal) can be provided to assist the user in easily identifying variants that are either unique or in common between pairs or sets of samples. For example, de novo mutations would be found in the child but not the parents in trios, or somatic mutations would be found in the tumor specimen but not its matched normal control. In various embodiments, the trio representation can be expanded to include more complex pedigrees.

Figure 12A:
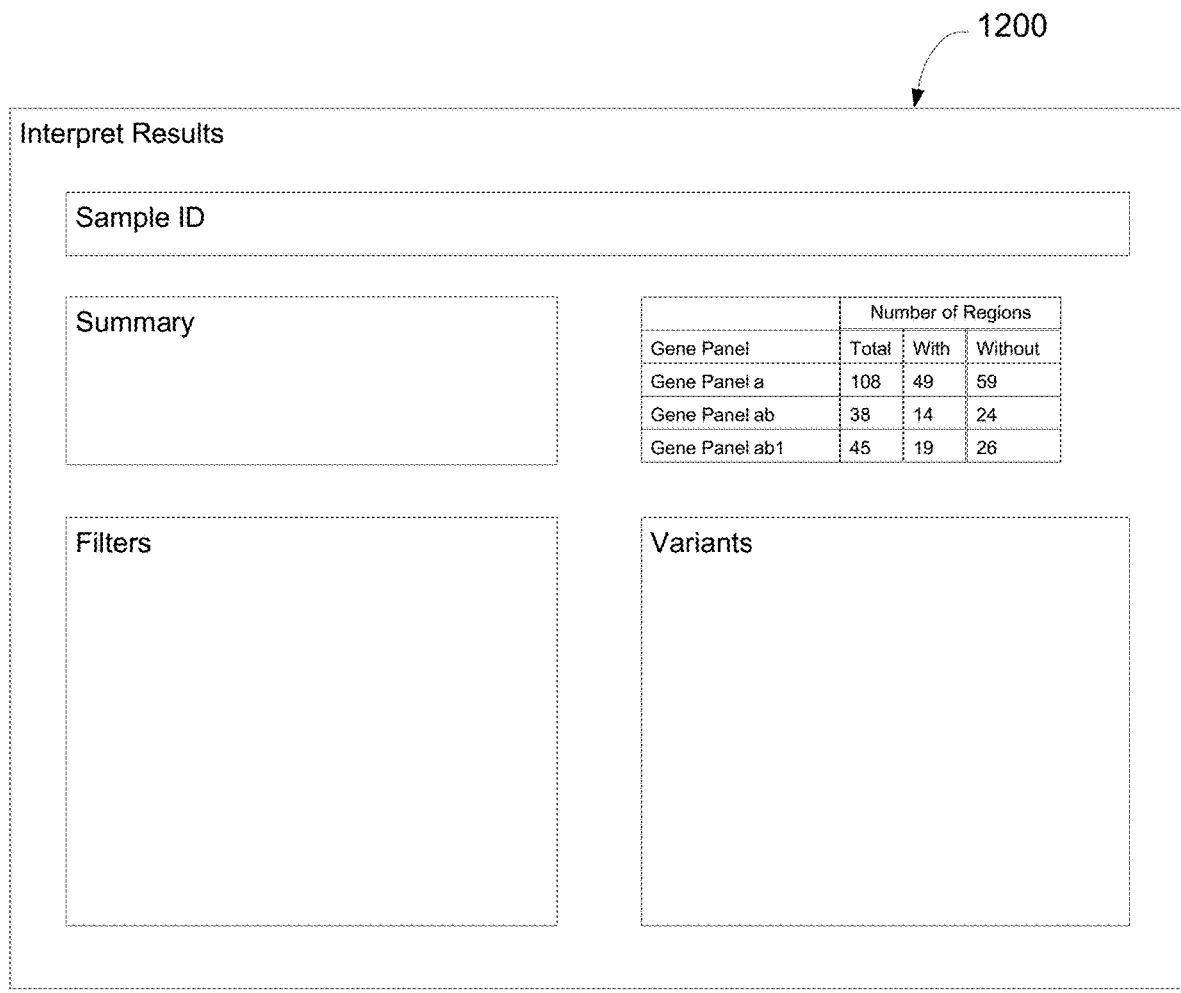
FIG. 12A is a diagram showing an exemplary interface for illustrating a gene panel, in accordance with various embodiments.

In various embodiments, variants from either single or multi sample analysis can be filtered based on their position relative to features (for example, genes or regions). FIG. 12A illustrates an exemplary interface 1200 showing that each gene panel is a non-overlapping collection of genomic regions that describe either the structures of single genes or an intergenic region of interest. When variant analysis is performed, variants may be found in some of these regions but not in others. This can enable partitioning of the gene panel into regions With Variants and regions Without Variants, which are mutually exclusive.

Figure 12B:
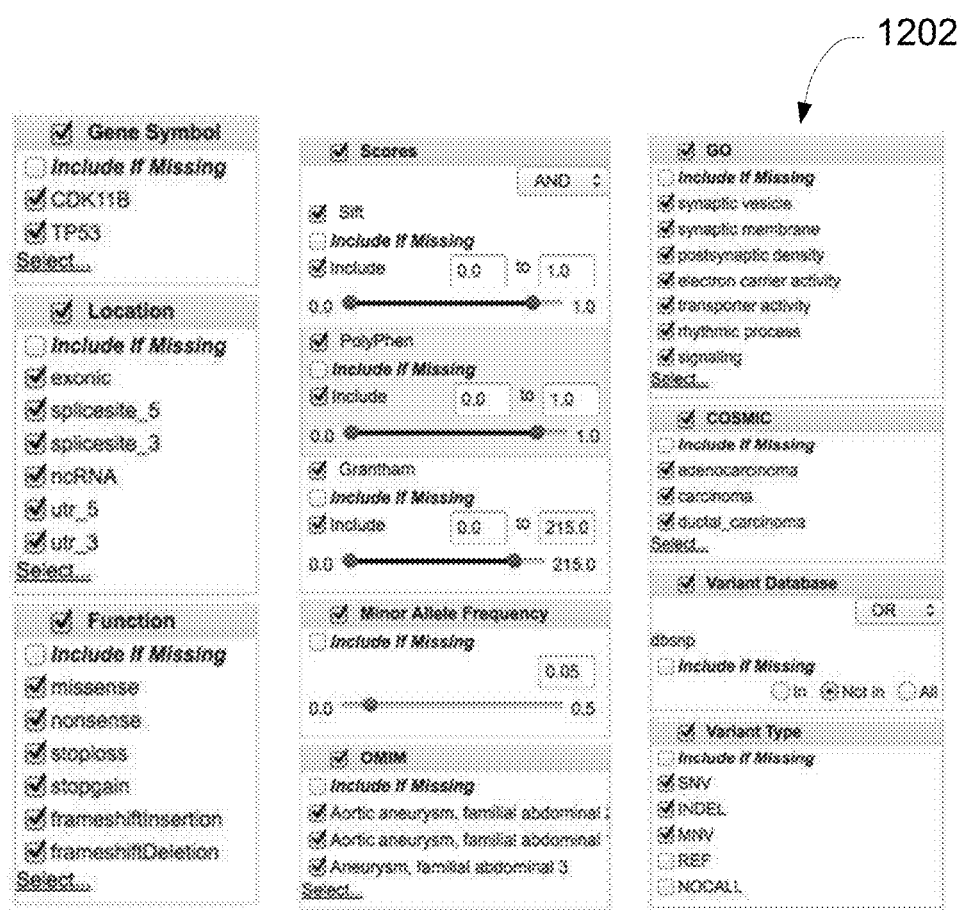
FIG. 12B is a diagram showing an exemplary interface for selecting variant filters, in accordance with various embodiments.

In various embodiments, the variants can be filtered base on a functional prediction score. For example, SIFT, Poly-Phen, and Grantham provide ways of assessing the effect of a particular amino acid change on the function or effectiveness of the protein. Typically the scores range from no effect (for example synonymous nucleotide change that does not affect the amino acid choice or a nonsynonymous nucleotide change between two amino acids with very similar properties like Lysine and Arginine) to a strong effect (introduction of a stop codon, creation or obliteration of a splicing site, change of an amino acid from small to large within a folded protein, change of an amino acid from polar/charged to non-polar/non-charged on the surface of the protein, a change to or from a cystine). For example, an interface can provide the user with slider to allow the selection of a range of scores to be used in the filtering process. FIG. 12B illustrates an exemplary interface 1202 for setting filters.

When the user has selected the appropriate filters and chosen the appropriate settings for the filters, the user can select to generate a report. In various embodiments, a selection of filters and their settings can be saved to be used to generate similar reports for other analysis. At 1114, the user can be presented with a preview of the report. Additionally, the user may add comments or a summary. Upon approval of the report, the user can publish the report at 1116.

Figure 13:
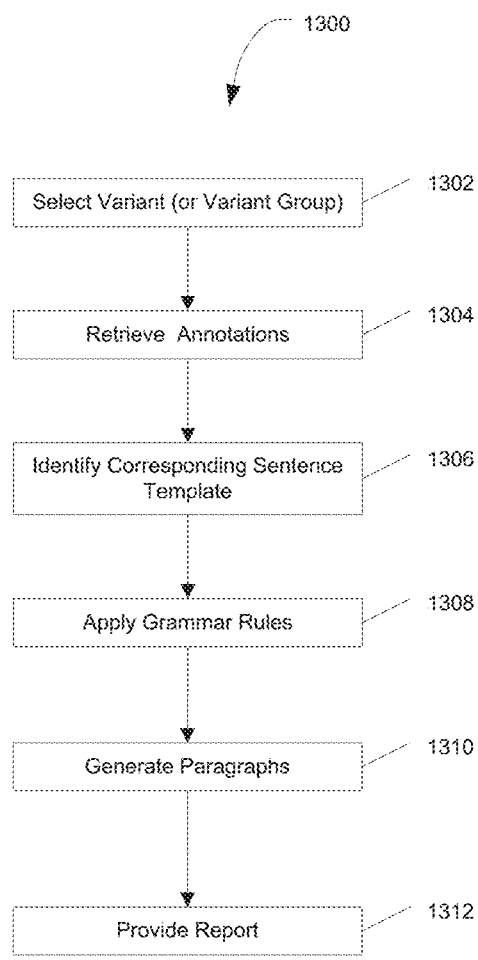
FIG. 13 is an exemplary flowchart showing a method for generating reports, in accordance with various embodiments.

FIG. 13 is an exemplary flowchart showing a method 1300 for generating a report, in accordance with various embodiments.

In step 1302, one or more variants are selected from a first data source, such as a variome data source. In various embodiments, the variome data store can be configured to store the variant in a format that is accessible for mining. In various embodiments, the variants can be selected by using filtering criteria to identify variants relevant to the report.

In step 1304, annotations associated with the selected variants can be received, and, in step 1306, sentence templates corresponding to the annotations can be identified. A sentence template can be a sentence structure with portions of the sentence defined and other portions of the sentence to be defined based on values associated with the variant or the annotation. For example, "(variant identifier) is in (gene identifier)" where the variant identifier and the identifier can be populated based on the variant and the annotation, or "(gene identifier) has been found to be related to (disease state) by (reference citation)" where the gene identifier, disease state, and reference citation can be populated based on variant and annotation information. In various embodiments, general sentence templates can be defined to correspond to different annotation types, such as by defining a functional type annotation sentence template and an interpretive type annotation sentence template. Further, sentence templates can be defined based on the level of annotation, such as allele level sentence template, gene level sentence templates, transcript level sentence templates, and the like. Still further, specific sentence templates can be defined for individual annotations or groups of annotations.

In step 1308, grammar rules can be applied to build the sentences. For example, grammar rules can be defined to select an appropriate article based on the information being inserted into a sentence template. Similarly, grammar rules can be defined to select an appropriate verb depending on whether an inserted noun is singular or plural. The grammar rules can be defined generally to apply to a group of sentence templates or a group of annotations, or specific grammar rules can be defined to make appropriate selections for problematic annotations.

In step 1310, paragraphs can be generated using annotations and the corresponding templates. For example, multiple sentence templates can be populated with the required information and structured into a paragraph. In various embodiments, paragraph rules can define how the sentence templates are arranged into the paragraph, such as which sentence templates occur earlier in the paragraph thereby defining a logical progression in the information or grouping of sentences by annotation source, specificity (such as allele, locus, transcript, gene, or the like), relevance, etc. For example, a sentence for identifying a gene may be required to be located before a sentence providing information about the gene, and sentences related to annotations from one annotation source may be grouped separately from sentences related to annotations from another annotation source.

Additionally, multiple paragraphs can be generated based on various groupings of annotations. For example, an allele paragraph can be generated to include allele level annotations for variants associated with an allele. Additionally, locus paragraphs, transcript paragraphs, gene paragraphs, etc, can be generated for relevant groups of variants to include annotation information relevant to the respective levels. For example, a gene paragraph can be generate to identify a gene in which one or more variants were identified and selected, and to provide information about the gene relevant to the report, rather than repeating the identity of the gene and the relevant information for each selected variant. In various embodiments, separate paragraphs can be generated for each annotation source, for each level of relevance, other groupings of sentences, or any combination thereof.

In step 1312, a report containing the paragraphs can be provided to a user, such as for review and editing, or for publication.

Figure 14:
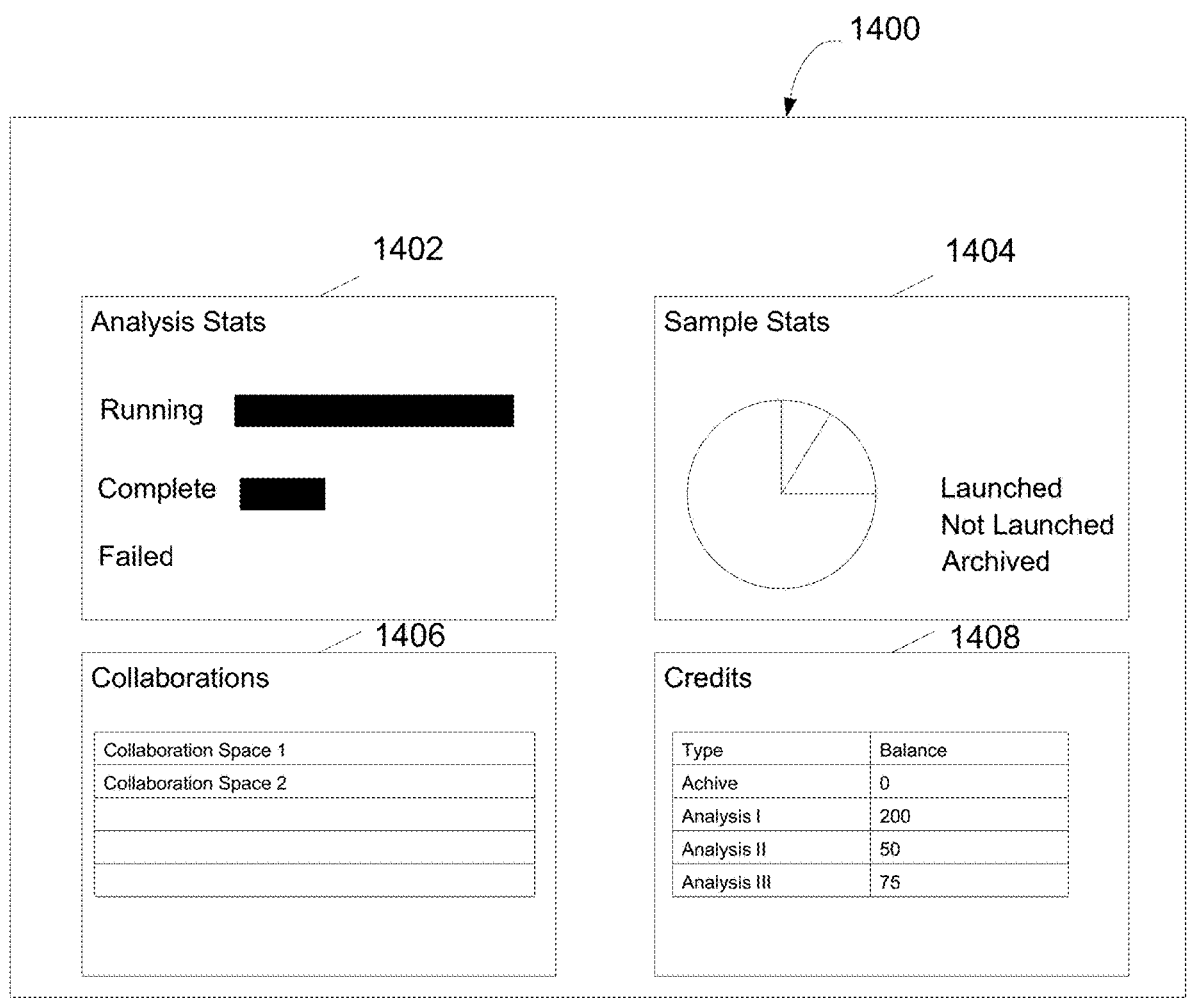
FIG. 14 is a diagram showing an exemplary interface for viewing status information for an account, in accordance with various embodiments.

FIG. 14 illustrates an exemplary interface 1400 for viewing the status of an account. From the status interface, a user can view the number of analyses that are running, complete, or failed (see 1402). Further, the user can view the number of samples where an analysis has been launched, the number of samples where an analysis has not been launched, and the number of samples that have been archived (see 1404). The status interface can also provide an indication of which collaboration spaces are active (see 1406), and account balances (see 1408).

In various embodiments, sets of general sentence templates can be predefined, and a user can define additional sentence templates, such as based upon review of the identified variants and resulting reports. For example, general sentence templates can be predefined to generate a report providing information related to the identified variants and user defined sentence templates can be defined to highlight significant diagnostic information when a particular variants is identified. Similarly, in various embodiments, sets of general grammar and paragraph rules can be predefined and the user can define additional grammar rules based upon review of the resulting reports. For example, the user may notice that the general grammar rules perform poorly in selecting an appropriate article for a particular annotation and may define a specific grammar rule to correctly select the article for that annotation. In various embodiments, new templates and rules can be defined by entering a template or rule or new templates and rules can be automatically generated by the system when a report is edited. In particular embodiments, when the templates or rules are automatically generated, the user may be presented with the automatically generate template or rule and given the option to modify, discard, or save the automatically generated template or rule.

In various embodiments, the methods of the present teachings may be implemented in a software program and applications written in conventional programming languages such as C, C++, etc.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over a network coupled computer systems so that the computer readable code is stored and executed in a distributed fashion.

What is claimed is:

1. A system, comprising:
a first data store configured to store genetic sequence information comprising called variants;
a second data store configured to store sequence annotation data; and
a processor communicatively connected with the first data store and the second data store, the processor configured to execute machine-readable instructions, which, when executed by the processor, cause the system to perform processing comprising:
receive the called variants from the first data store,
receive functional type annotations from the second data store, wherein the functional type annotations include an indication of a change in an amino acid sequence, an indication of a change in an expression level of a protein and an indication of a change in a splicing of a transcript,
receive interpretive type annotations from the second data store,
normalize genomic coordinates of the functional type annotations and the interpretive type annotations to form normalized genomic coordinates for the functional type annotations and the interpretive type annotations,
assign positions to the called variants in accordance with the normalized genomic coordinates,
associate functional type annotations with the called variants based on the normalized genomic coordinates,
update the called variants in the first data store with the associated functional type annotations,
associate interpretive type annotations with the called variants based on the normalized genomic coordinates,
update the called variants in the first data store with the associated interpretive type annotations,
configure a user interface on a user electronic device to display variant filter conditions selectable by a user of the electronic device,
receive a set of user-selected variant filter conditions,
query the first data store based on the set of user-selected variant filter conditions, and
generate a report of the called variants based on at least one of functional annotations and interpretive annotations obtained from results of querying the first data store.

2. The system of claim 1, wherein the first data store includes an indexed database table of the called variants.

3. The system of claim 1, wherein the functional type annotation includes a listing of transcripts impacted by the called variant.

4. The system of claim 3, wherein the functional type annotation includes a protein function impact score for the called variant.

5. The system of claim 4, wherein the functional type annotation includes base information for codons associated with the called variant.

6. The system of claim 1, wherein the interpretive type annotation includes an association of the called variant with a disease, a correlation between the called variant and a response to a treatment, metabolic pathways impacted by the called variant, a biological signaling pathway impacted by the called variant, a regulation pathway impacted by the called variant or a match to a list of annotated variants.

7. The system of claim 1, wherein the interpretive type annotation includes a metabolic pathway impacted by the called variant, a biological signaling pathway impacted by the called variant or a regulation pathway impacted by the called variant.

8. The system of claim 1, wherein the processor is further configured to perform processing comprising: group the called variants that fall within blocks of overlapping transcripts together into a gene block and to annotate the called variants of the gene block at the same time.

9. The system of claim 1, wherein the processor is further configured to perform processing comprising:
receive annotations information having an original format from an external annotations source;
convert the annotations information from the original format to a format compatible with a database structure of the second data store, and
store the converted annotations information to a database in the second data store.

10. A computer-implemented method, comprising:
receiving called variants from a first data store configured to store genetic sequence information comprising the called variants;
receiving functional type annotations from a second data store, wherein the functional type annotations include an indication of a change in an amino acid sequence, an indication of a change in an expression level of a protein and an indication of a change in a splicing of a transcript;
receiving interpretive type annotations from the second data store;
normalizing genomic coordinates of the functional type annotations and the interpretive type annotations to form normalized genomic coordinates for the functional type annotations and the interpretive type annotations;
assigning positions to the called variants in accordance with the normalized genomic coordinates;
associating the functional type annotations with the called variants based on the normalized genomic coordinates;
updating the called variants in the first data store with the associated functional type annotations;
associating interpretive type annotations with the called variants based on the normalized genomic coordinates;
updating the called variants in the first data store with the associated interpretive type annotations;
configuring a user interface on a user electronic device to display variant filter conditions selectable by a user of the electronic device,
receiving a set of user-selected variant filter conditions,
querying the first data store based on the set of user-selected variant filter conditions, and
generating a report of the called variants based on at least one of functional annotations and interpretive annotations obtained from results of querying the first data store.

11. The method of claim 10, wherein the functional-type annotation includes a listing of transcripts impacted by the called variant.

12. The method of claim 10, wherein the functional-type annotation includes a protein function impact score for the called variant.

13. The method of claim 12, wherein the functional-type annotation includes base information for codons associated with the called variant.

14. The method of claim 10, wherein the interpretive type annotation includes an association of the called variant with a disease, a correlation between the called variant and a response to a treatment, metabolic pathways impacted by the called variant, a biological signaling pathway impacted by the called variant, a regulation pathway impacted by the called variant or a match to a list of annotated variants.

15. The method of claim 10, wherein the interpretive type annotation includes a metabolic pathways impacted by the called variant, a biological signaling pathway impacted by the called variant or a regulation pathway impacted by the called variant.

16. The method of claim 10 further comprising grouping the called variants that fall within blocks of overlapping transcripts together into a gene block and annotating the called variants of the gene block at the same time.

17. The method of claim 10, further comprising:
receiving annotations information having an original format from an external annotations source;
converting the annotations information from the original format to a format compatible with a database structure of the second data store; and
storing the converted annotations information to a database in the second data store.

18. The method of claim 10, wherein the first data store includes an indexed database table of the called variants.

* * * * *

UNITED STATES PATENT AND TRADEMARK OFFICE
CERTIFICATE OF CORRECTION

| | | |
|---|---|---|
| PATENT NO. | : 10,937,522 B2 | Page 1 of 1 |
| APPLICATION NO. | : 16/211609 | |
| DATED | : March 2, 2021 | |
| INVENTOR(S) | : Brijesh Krishnaswami et al. | |

It is certified that error appears in the above-identified patent and that said Letters Patent is hereby corrected as shown below:

In the Claims

Column 29, Claim 15, Line 5: delete "a metabolic pathways" and insert --a metabolic pathway--, therefor.

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*